United States Patent
Zhong

(10) Patent No.: US 11,667,914 B2
(45) Date of Patent: *Jun. 6, 2023

(54) CHEMICALLY LIGATED RNAS FOR CRISPR/CAS9-1GRNA COMPLEXES AS ANTIVIRAL THERAPEUTIC AGENTS

(71) Applicant: Minghong Zhong, Sellersville, PA (US)

(72) Inventor: Minghong Zhong, Sellersville, PA (US)

(*) Notice: Subject to any disclaimer, the term of this patent is extended or adjusted under 35 U.S.C. 154(b) by 1027 days.

This patent is subject to a terminal disclaimer.

(21) Appl. No.: 16/029,653

(22) Filed: Jul. 9, 2018

(65) Prior Publication Data
US 2018/0305688 A1  Oct. 25, 2018
US 2022/0290135 A9  Sep. 15, 2022

Related U.S. Application Data

(63) Continuation of application No. 15/006,131, filed on Jan. 26, 2016, now Pat. No. 10,059,940.

(60) Provisional application No. 62/108,064, filed on Jan. 27, 2015.

(51) Int. Cl.
| | |
|---|---|
| C12N 15/11 | (2006.01) |
| C12N 15/113 | (2010.01) |
| A61K 38/17 | (2006.01) |
| A61K 31/7105 | (2006.01) |
| C12N 9/96 | (2006.01) |
| A61K 38/00 | (2006.01) |

(52) U.S. Cl.
CPC ........ *C12N 15/111* (2013.01); *A61K 31/7105* (2013.01); *A61K 38/1709* (2013.01); *C12N 9/96* (2013.01); *C12N 15/11* (2013.01); *C12N 15/1132* (2013.01); *A61K 38/00* (2013.01); *C12N 2310/10* (2013.01); *C12N 2310/20* (2017.05); *C12N 2310/3519* (2013.01); *C12N 2320/30* (2013.01)

(58) Field of Classification Search
None
See application file for complete search history.

(56) References Cited

U.S. PATENT DOCUMENTS

| | | | | |
|---|---|---|---|---|
| 10,059,940 B2* | 8/2018 | Zhong | ............... | C12N 15/111 |
| 2013/0046083 A1 | 2/2013 | Brown | | |
| 2014/0068797 A1* | 3/2014 | Doudna | ............... | A01H 6/4684 |
| | | | | 435/375 |
| 2014/0179770 A1 | 6/2014 | Zhang | | |
| 2014/0243348 A1* | 8/2014 | Knipe | ............... | A61K 31/513 |
| | | | | 514/250 |
| 2015/0376583 A1* | 12/2015 | Quake | ............... | A61K 48/005 |
| | | | | 424/94.6 |
| 2016/0040189 A1* | 2/2016 | Kennedy | ............ | C12N 15/102 |
| | | | | 252/189 |
| 2016/0102322 A1 | 4/2016 | Ravinder | | |
| 2016/0348074 A1* | 12/2016 | Quake | ............... | C12N 9/22 |
| 2017/0020994 A1* | 1/2017 | Bloom | ............... | C12N 9/22 |
| 2017/0073685 A1 | 3/2017 | Maeder | | |

FOREIGN PATENT DOCUMENTS

WO   WO-2013176844 A1 * 11/2013   ............... C07H 1/00

OTHER PUBLICATIONS

Roizman et al. Herpes Simplex viruses in Field Virology, DM Knipe, Howley, PM, editor Philadelphia: lippincott williams and wilkins 2501-2548 (Year: 2007).*
Roizman et al. Herpes Simplex viruses in Field Virology, DM Knipe, Howley, PM, editor Philadelphia: lippincott williams and wilkins 2549-2601 (Year: 2007).*
Konermann et al. Nature 517, 583-588, pp. 1-18 (Year: 2015).*
Paredes et al. ChemBioChem 12, 125-131 (Year: 2011).*
Mieghdad Rahdar, et al. Synthetic CRISPR RNA-Cas9-guided genome editing in human cells. PNAS 2015, E7110-E7117.
Ayal Hendel, et al. Chemically modified guide RNAs enhance genome editing in human primary cells. Nature biotechnology 2015, 33, 985-989.
Hiroshi Nishimasu, et al. Crystal Structure of Cas9 in Complex with Guide RNA and Target DNA. Cell 2014, 156, 935-949.
Martin Jinek, et al. A Programmable Dual-RNA—Guided DNA Endonuclease in Adaptive Bacterial Immunity. Science 2012, 337, 816-821.
Yanfang Fu, et al. High-frequency off-target mutagenesis induced by CRISPR-Cas nucleases in human cells. Nature biotechnology 2013, 31, 822-826.
Kaizhang He, et al. Conjugation and Evaluation of Triazole-Linked Single Guide RNA for CRISPR-CasQ Gene Editing. ChemBioChem 2016, 17, 1800-1812.

* cited by examiner

*Primary Examiner* — Brian Whiteman

(57) ABSTRACT

Provided herein are chemically ligated guide RNA oligonucleotides (lgRNA) which comprise two functional RNA modules (crgRNA and tracrgRNA) joined by non-nucleotide chemical linkers (nNt-linker), their complexes with CRISPR-Cas9, preparation methods of Cas9-lgRNA complexes, and their uses for prevention and treatments of herpesvirus infections in humans. Also disclosed are processes and methods for preparation of these compounds.

22 Claims, 4 Drawing Sheets

Specification includes a Sequence Listing.

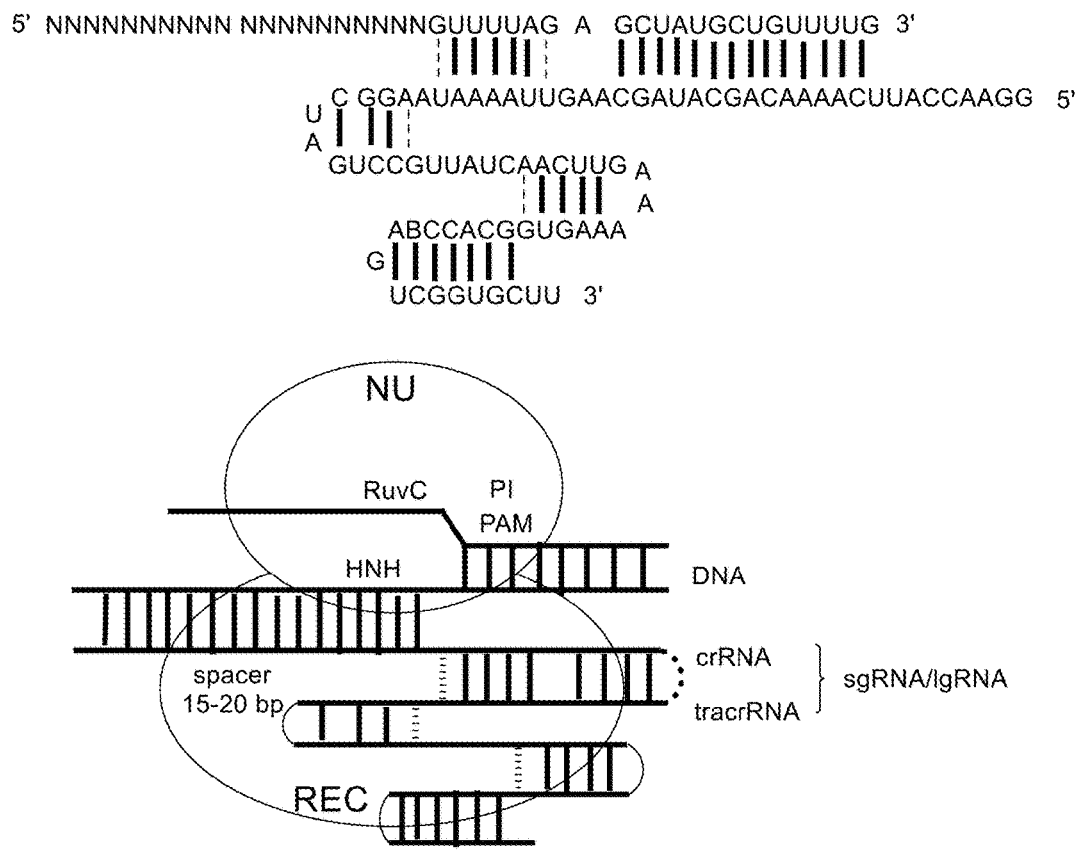
Figure 1. crRNA/tracrRNA (Streptococcus Pyogenes Cas, Top); Model of sg/lgRNA-Cas9 complex (Bottom)

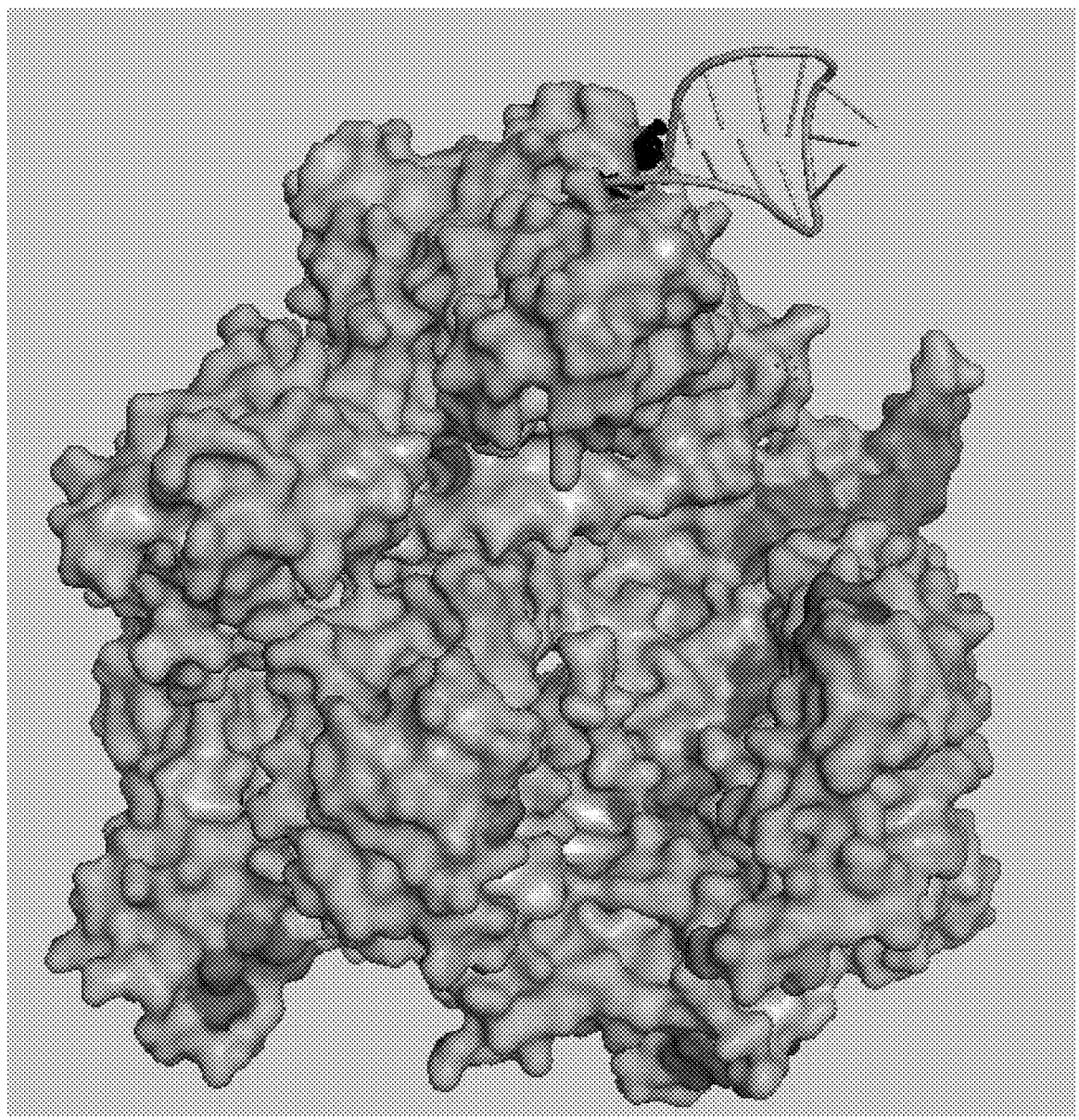
Figure 2. Cas9:sgRNA complex (PyMOL)

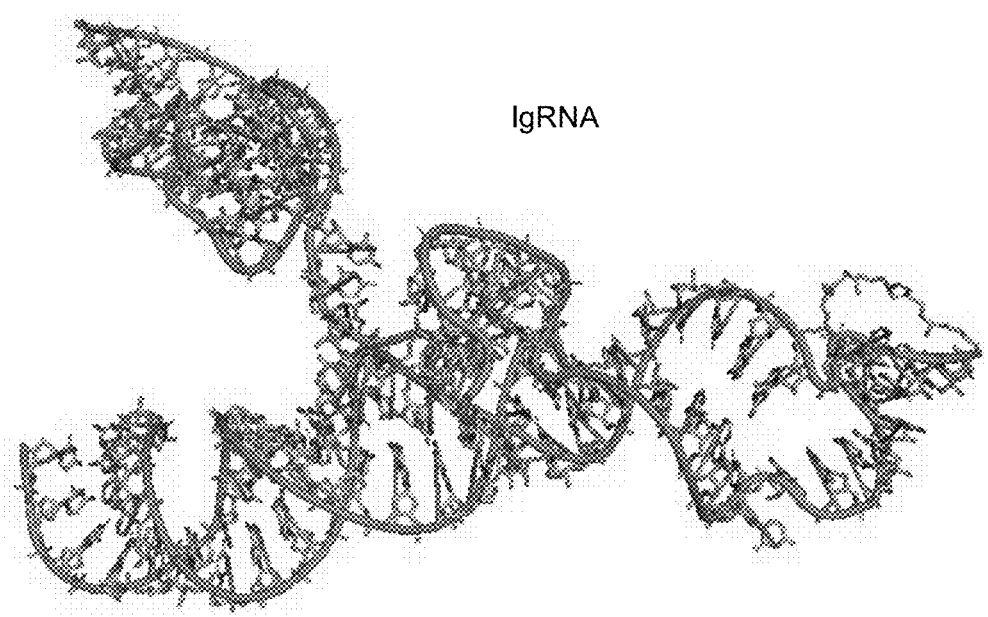
Figure 3. Model of lgRNA

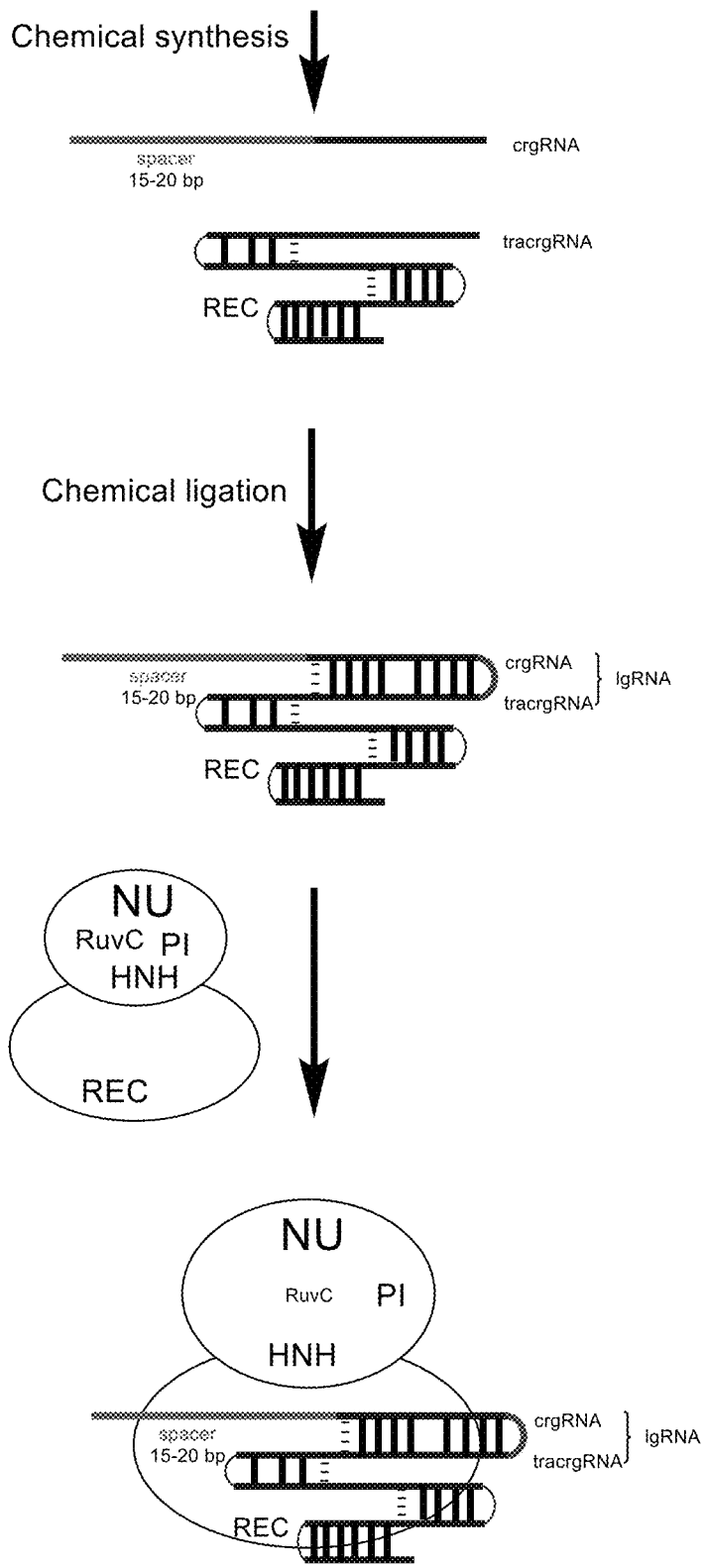
Figure 4. Formation of lgRNA and assemble of lgRNA:Cas9 complex

CHEMICALLY LIGATED RNAS FOR CRISPR/CAS9-1GRNA COMPLEXES AS ANTIVIRAL THERAPEUTIC AGENTS

CROSS REFERENCE TO RELATED APPLICATIONS

The present application is a continuation application of U.S. application Ser. No. 15/006,131, filed Jan. 26, 2016, with title "Chemically Ligated RNAs for CRISPR/Cas9-lgRNA Complexes as Antiviral Therapeutic Agents" and naming Minghong Zhong as inventor(s), and claims the benefits of U.S. Provisional Application Ser. No. 62/108,064, the entire said invention being incorporated herein by reference.

INCORPORATION BY REFERENCE OF SEQUENCE LISTING

The contents of the sequence listing text named "lgRNA_anti_HSV.txt", which was created on Nov. 11, 2022, and 15233 bytes in size, are incorporated herein by reference in its entirety.

TECHNICAL FIELD OF THE INVENTION

The present invention relates to chemically synthesized guide RNA oligonucleotides (lgRNA) comprising two functional RNA modules (crgRNA and tracrgRNA) ligated by non-nucleotide chemical linker(s) (nNt-linker), their complexes with CRISPR-Cas9, preparation methods of Cas9-lgRNA complexes, and uses as medicinal agents in treatment of chronic viral infections.

BACKGROUND OF THE INVENTION

Chronic viral infections such as HIV, HBV, and HSV afflict enormous suffering, life loss, and financial burdening among the infected individuals. These infectious diseases are incurable, and contagious to variable degrees, and are prominent threats for public health, highlighting the urgent needs for curative therapies. To date, effective antiviral therapies only suppress viral replication but do not clear virus in patients, and do not target the viral genetic materials of latently integrated (proviral DNA) or non-replicating episomal viral genomes (such as cccDNA) in human cells. Nevertheless, these viral DNAs have been reported to directly cause these chronic or latent infections.

Recent breakthroughs in biotechnology have identified several molecular gene editing tools such as zinc finger nucleases (ZFNs), transcription activator-like (TAL) effector nucleases (TALENs), homing endonucleases (HEs), and most notably the clusters of regularly interspaced short palindromic repeat (CRISPR)-associated protein Cas9. These nucleases are highly specific, DNA-cleaving enzymes, and have been recently demonstrated as potential therapeutic applications to eradicate HBV, HIV, HSV, and herpesvirus by targeting the enzymatic systems directly to essential viral genome sequences.

Both ZFNs and TALENs are composed of protein-based programmable, sequence-specific DNA-binding modules and nonspecific DNA cleavage domains, which make multiple-site targeting extremely challenging. This is even more challenging for HEs, which have the same protein domains for both DNA binding and cleavage.

Unlike nucleases such as ZFNs, TALENs, and HEs, CRISPR-Cas-RNA complexes contain short CRISPR RNAs (crRNAs), which direct the Cas proteins to the target nucleic acids via Watson-Crick base pairing to facilitate nucleic acid destruction. Three types (I-III) of CRISPR-Cas systems have been functionally identified across a wide range of microbial species. While the type I and III CRISPR systems utilize ensembles of Cas proteins complexed with crRNAs to mediate the recognition and subsequent degradation of target nucleic acids, the type II CRISPR system recognizes and cleaves the target DNA via the RNA-guided endonuclease Cas9 along with two noncoding RNAs, the crRNA and the trans-activating crRNA (tracrRNA). The crRNA::tracrRNA complex directs Cas9 DNA endonuclease to the protospacer on the target DNA next to the protospacer adjacent motif (PAM) for site-specific cleavage (FIG. 1). This system is further simplified by fusing the crRNA and tracrRNA into a single chimeric guide RNA (sgRNA) with enhanced efficiency, and can be easily reprogrammed to cleave virtually any DNA sequence by redesigning the crRNAs or sgRNAs.

The CRISPR/Cas9 system has been evaluated as potential therapeutic strategy to cure chronic and/or latent viral infections such as HIV, HBV, and Epstein-Barr virus (EBV). Hu and et al. reported CRISPR/Cas9 system could eliminate the integrated HIV-1 genome by targeting the HIV-1 LTR U3 region in single and multiplex configurations. It inactivated viral gene expression and replication in latently infected microglial, promonocytic, and T cells, completely excised a 9,709-bp fragment of integrated proviral DNA that spanned from its 5' to 3' LTRs, and caused neither genotoxicity nor off-target editing to the host cells. Yang and et al. reported the CRISPR/Cas9 system could significantly reduce the production of HBV core and surface proteins in Huh-7 cells transfected with an HBV-expression vector, and disrupt the HBV expressing templates both in vitro and in vivo, indicating its potential in eradicating persistent HBV infection. They observed that two combinatorial gRNAs targeting different sites could increase the efficiency in causing indels. The study by Seeger and Sohn also reported CRISPR/Cas9 efficiently inactivated HBV genes in NTCP expressing HepG2 cells permissive for HBV infection. Wang and Quake observed patient-derived cells from a Burkitt's lymphoma with latent Epstein-Barr virus infection presented dramatic proliferation arrest and a concomitant decrease in viral load after exposure to a CRISPR/Cas9 vector targeted to the viral genome and a mixture of seven guide RNAs at the same molar ratio via plasmid.

In spite of initial success in evaluation of CRISPR/Cas9 for therapeutic applications in treatment of chronic or latent viral infections, off-target cleavage is a major concern for any nuclease therapy. Studies indicated that a 10-12 bp "seed" region located at the 3'-end of the protospacer sequence is critical for its site-specific cleavage, and that Cas9 can tolerate up to seven mismatches at the 5'-end of the 20-base protospacer sequence.

Cas9::sgRNA was reported to be a single turnover enzyme, and was tightly bound by the cleaved DNA products. In thermodynamic term, the energetic increase in the unwound DNA helix (two DNA single strand) in Cas9 is compensated by free energy decrease of the hybridization between DNA and crRNA and of the binding of Cas9 with the formed DNA:crRNA helix and with the resulting single strand DNA; to release the cleaved DNA products, especially the hybridized DNA strand with crRNA, the free energy increase in the released DNA requires compensation of free energy decrease by certain processes such as binding of additional protein factor(s), enabling the recycling of the Cas::sgRNA enzyme, which is believed to happen under physiological conditions. A more related but also more complicated in vitro assay comprising both Cas9::sgRNA and other binding molecules or cellular assay is needed for reliable SAR based on multiple turnover enzymatic reactions.

Another major concern is the requirement of more sophisticated approaches to delivery. To date, the Cas9 protein and RNAs (either dualRNA (crRNA/tracrRNA) or a single guide RNA (sgRNA, ~100 nt)) have been mostly introduced by plasmid transfection either as whole or separately, which makes chemical modifications of RNAs extremely challenging, if not impossible, and also is limited by random integration of all or part of the plasmid DNA into the host genome and by persistent and elevated expression of Cas9 in target cells that could lead to off-target effects. A recent study presented lipid-mediated delivery of unmodified Cas9::sgRNA complexes using common cationic lipid nucleic acid transfection reagents such as Lipofectamine resulted in up to 80% genome modification with substantially higher specificity compared to DNA transfection, and be effective both in vitro and in vivo. Another example presented treatment with cell penetrating peptide (CPP)-conjugated recombinant Cas9 protein and CPP-complexed guide RNAs led to endogenous gene disruptions in human cell lines with lower off-target mutation frequencies than plasmid transfection.

To minimize or completely eradicate off-target effects, and to overcome other major obstacles to its pharmaceutical applications including the lack of stability of RNA, low potency of Cas9-gRNA at the target sites, large sizes of Cas9 proteins (~150 kDa), chemically modified sgRNAs may provide a very effective strategy as indicated by the therapeutic application of antisense oligonucleotides and progress in small interfering RNA technology, and also supported by a recent report on chemically modified, 29-nucleotide synthetic CRISPR RNA (scrRNA) in combination with unmodified transactivating crRNA (tracrRNA), showing a comparable efficacy as sgRNA, though as dual guide RNAs, this combination should be less effective than sgRNA incorporated with same chemical modifications because of entropic and other factors. However, considering the size of sgRNA (~100 nt), large scale chemically manufacturing such large molecules is industrially challenging and costly. Methods for preparation of long RNAs (sgRNA) compatible to extensive chemical modifications and/or significantly truncated sgRNAs or crRNA/tracrRNAs of lengths compatible to current industrial RNA chemical synthesis are in need. Truncating sgRNAs or crRNA/tracrRNAs is limited because of the many essential binding interactions between Cas9 and sgRNA and the complicated molecular mechanisms of recognition and cleavage of target DNAs. A possible solution can be based on recent progress in chemical ligations of nucleic acids. Brown and et al. showed the CuAAC reaction (click chemistry) in conjunction with solid-phase synthesis could produce catalytically active hairpin ribozymes around 100 nucleotides in length.

Recent disclosure of the structure of CRISPR/Cas9-sgRNA complexes indicated that the linkloop (tetraloop) of the sgRNA protrudes outside of the CRISPR/Cas9-sgRNA complex, with the distal 4 base pairs (bp) completely free of interactions with Cas9 peptide side chains (FIG. 2). The natural guide RNAs comprise CRISPR RNA (crRNA) and trans-activating crRNA (tracrRNA), directing Cas9 to a specific genomic locus harboring the target sequence, in spite of their lower efficacy than sgRNA. Therefore this tetraloop can be replaced by small molecule non-nucleotide linkers (nNt-linker), and sgRNA can be divided into two pieces of ~30-32 nt (crgRNA) and ~60 nt (tracrgRNA) (FIG. 3), respectively, or into three pieces (~30-32 nt (crgRNA), ~30 nt (tracrgRNA1), and ~30 nt (tracrgRNA2)), or multiple pieces based on the void of interactions between certain other sections of sgRNA and Cas9, and joined by chemical ligations in vitro as ligated guide RNAs (lgRNA). These RNAs (crgRNA and tracrgRNA) are more readily synthesized chemically at industrial scale, and can even be further shortened by introductions of chemical modifications at various sites, and therefore more commercially accessible, and lgRNAs can be optimized by chemical modifications for better efficacy and specificity and for targeted delivery.

As presented by previous studies, targeting viral DNA at multiple sites could enhance the effectiveness, which can be better practiced by delivering whole CRISPR/Cas9-lgRNA complexes composed of chemical libraries of different crgRNAs (including various spacers) and formed in vitro. This chemical ligation strategy can provide diverse chemically modified lgRNAs targeting multiple sites and/or variants/mutations of a single site in viral genomes equivalent to combination therapies such as HAART.

SUMMARY OF THE INVENTION

This invention pertains to chemically ligated guide RNA oligonucleotides (lgRNA) comprising two functional RNA modules (crgRNA and tracrgRNA, or crgRNA and dual-tracrgRNA or multiple-tracrgRNA) joined by chemical nNt-linkers, their complexes with CRISPR-Cas9, preparation methods for Cas9-lgRNA complexes and their uses in the treatments of viral infections in humans, represented by the following structure (Formula I):

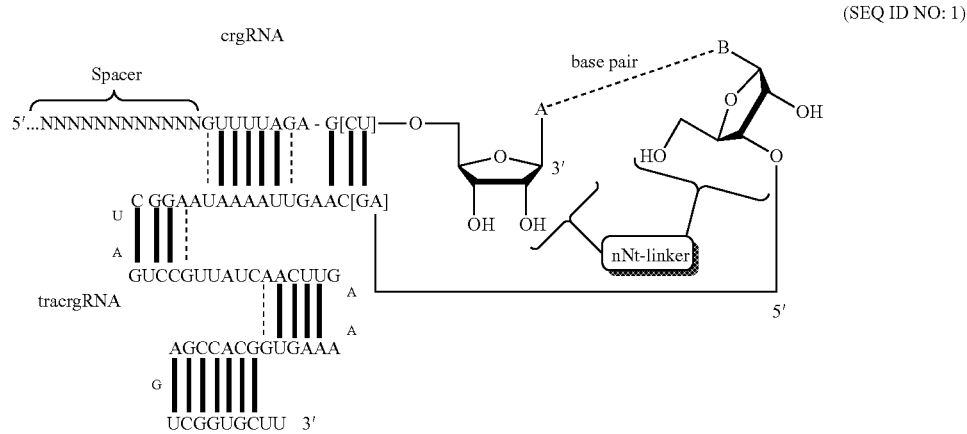

(SEQ ID NO: 1)

wherein (a) spacer NNNNNNNNNNNNN . . . ) is an oligonucleotide derived from viral genomes corresponding to a viral DNA sequence (protospacer) immediately before NGG or any of other protospacer adjacent motifs (PAM);

(b) spacers NNNNNNNNNNNNN . . . ) comprise nucleotides modified at sugar moieties such as 2'-deoxyribonucleotides, 2'-methoxyribonucleotides, 2'-F-ribonucleotides, 2'-F-arabinonucleotides, 2'-O,4'-C-methylene nucleotides (LNA), unlocked nucleotides (UNA), nucleoside phosphonoacetate (PACE), thiophosphonoacetate (thioPACE), and phosphoromonothioates:

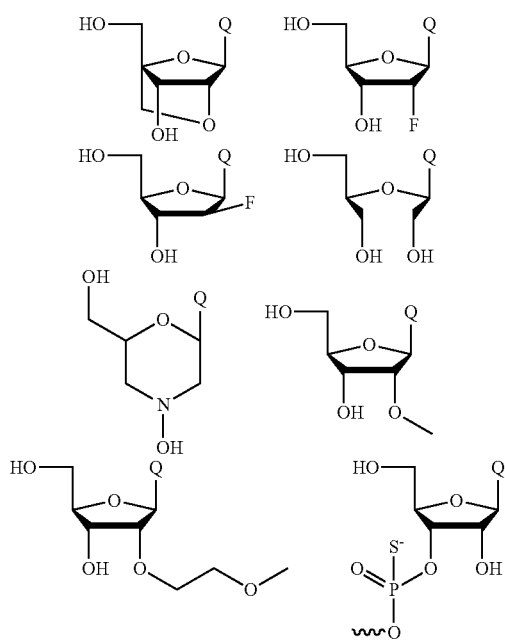

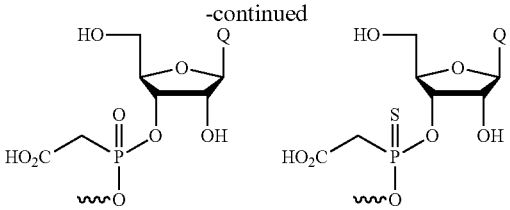

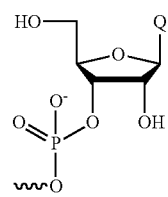

wherein Q is a nucleic acid base;

(c) A . . . B base pair is selected from A . . . U, U . . . A, C . . . G, and G . . . C;

(d) "nNt-Linker" is a chemical moiety joining the 3'-end of crgRNA and 5'-end of tracrgRNA, and is constructed by click chemistry or chemical ligations; the attaching position at the 3'-end nucleotide of crgRNA can be selected from 3'-, 2'-, and 7- (for 7-deazapurinenucleoside) or 5- (for pyrimidine nucleosides) or 8- (for purine nucleosides) positions, and the attaching position at the 5'-end nucleotide of tracrgRNA can be selected from 5'-, 2'-, and 7- (for 7-deazapurinenucleoside) or 5- (for pyrimidine nucleosides) or 8- (for purine nucleosides) positions, as represented by non-limiting examples below:

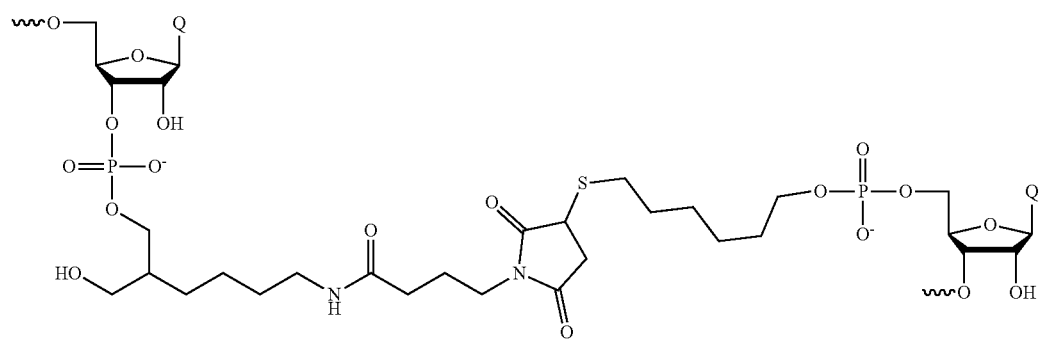

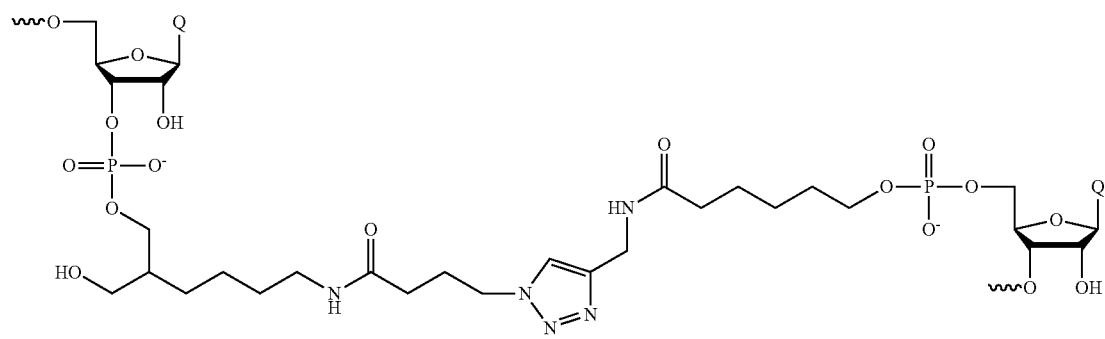

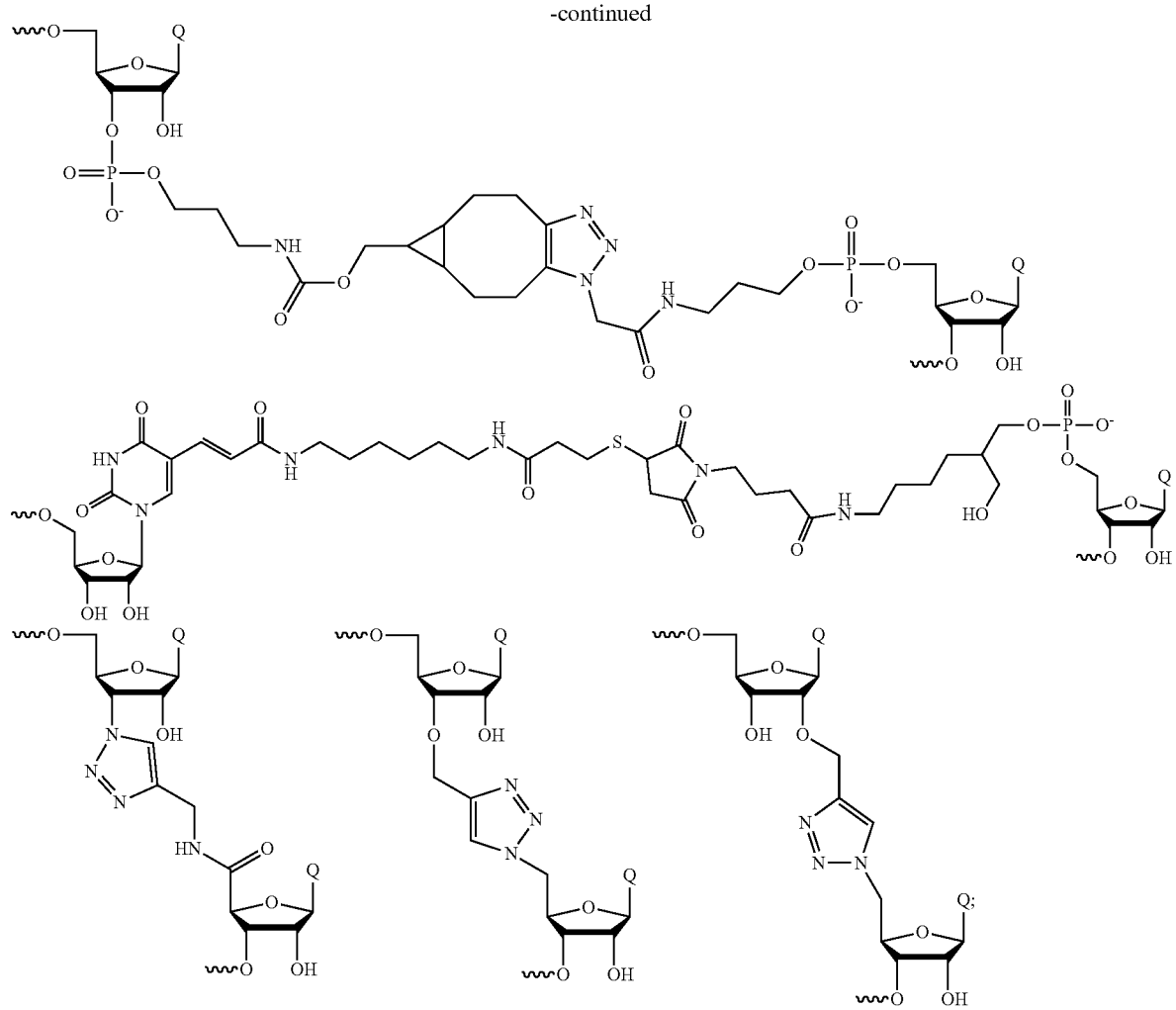
40
(d) Nucleotides in [ ] ([CU] and [GA]) can be deleted or replaced with other nucleotides preferably with base pair(s) unaffected with or without modifications of sugar moieties;
(e) The Cas9-lgRNA complexes can be prepared in the following steps (FIG. 4):
Step 1. Synthesis of crgRNA and tracrgRNA. Structures of non-limiting examples are given below:
(SEQ ID NO: 2)
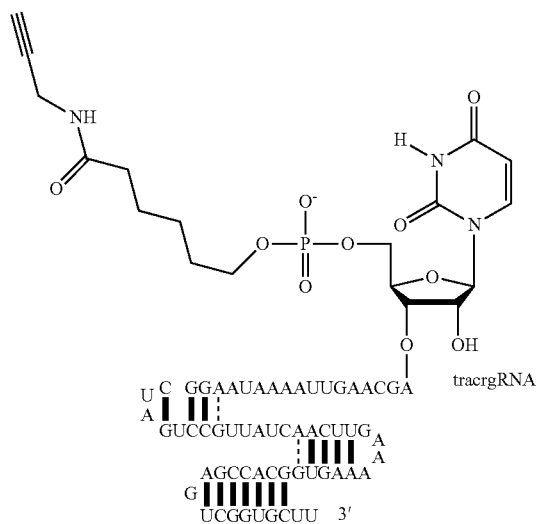

(SEQ ID NO: 3)

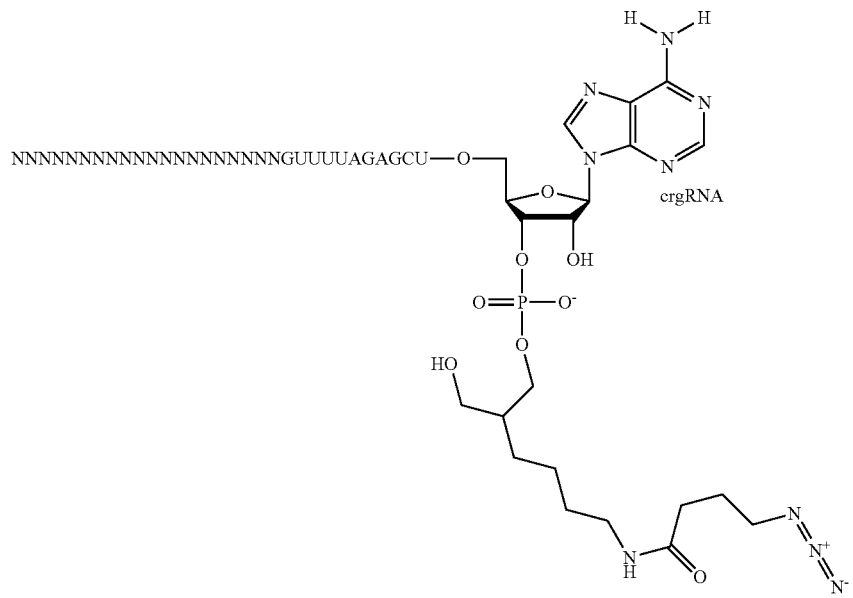

Step 2. Chemical ligation of crgRNA and tracrgRNA and annealing to form RNA duplex, lgRNA:

(SEQ ID NO: 4)

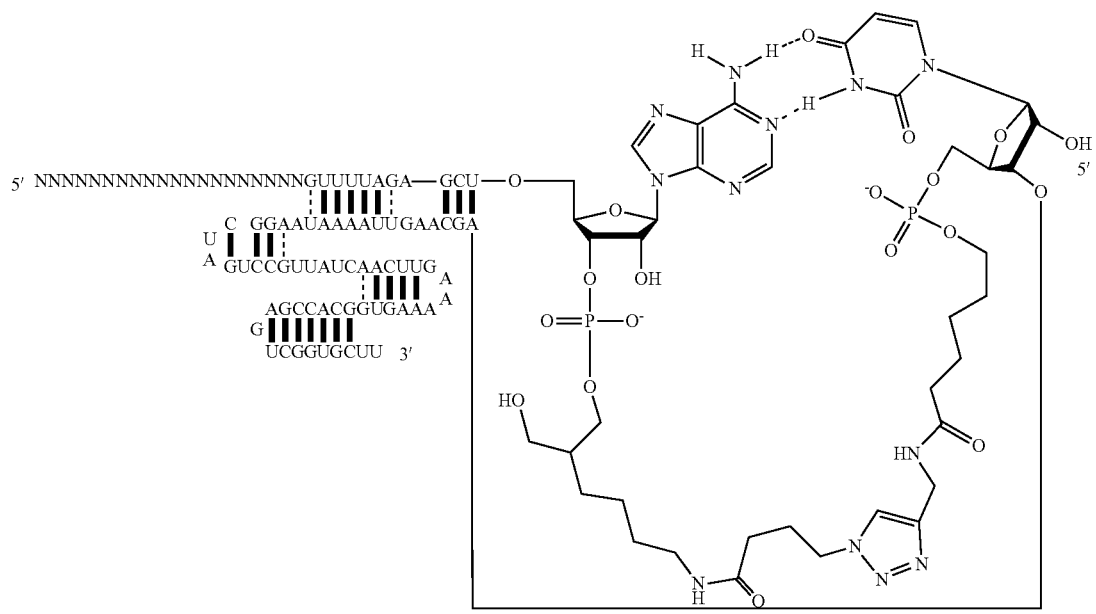

or annealing followed by chemical ligation to form lgRNA.

Step 3. In vitro complex formation between lgRNA and Cas9 protein.

(f) crgRNA in (e) can be single oligonucleotide or a mixture of oligonucleotides of various sequences, and thus the preparation gives a mixture of combinatorial Cas9-lgRNA complexes targeting multiple sites in viral genomes.

In some embodiments, tracrgRNA is a single RNA with chemical modifications or without chemical modifications. In some embodiments, tracrgRNA is a ligated dual oligonucleotide, comprising tracrgRNA1 and tracrgRNA2, or a multiple oligonucleotides.

Provided herein are chemically ligated oligonucleotides for CRISPR-Cas9, their complexes with CRISPR-Cas9, preparation methods and uses of these complexes as medicinal agents in treatment of viral infections. Embodiments of these structures, preparations, and applications are described in details herein.

In certain embodiments, lgRNAs comprise modified nucleotides in crgRNAs, and non-limiting examples include 2'-deoxyribonucleotides, 2'-methoxyribonucleotides, 2'-F-ribonucleotides, 2'-F-arabinonucleotides, 2'-methoxyethoxyribonucleotides, 2'-O,4'-C-methylene nucleotides (LNA), unlocked nucleotide analogues (UNA), nucleoside phosphonoacetate (PACE), thiophosphonoacetate (thioPACE), and phosphoromonothioates[[;]].

In certain embodiments, lgRNAs comprise modified nucleotides in tracrgRNAs, and non-limiting examples include 2'-deoxyribonucleotides, 2'-methoxyribonucleotides, 2'-F-ribonucleotides, 2'-F-arabinonucleotides, 2'-methoxyethoxyribonucleotides, 2'-O,4'-C-methylene nucleotides (LNA), unlocked nucleotide analogues (UNA), nucleoside phosphonoacetate (PACE), thiophosphonoacetate (thioPACE), and phosphoromonothioates.

In certain embodiments, lgRNAs comprise nucleotides modified in base moieties of tracrgRNAs, and non-limiting examples include 2,6-diaminopurine, 5-fluorouracil, pseudouracil, and 7-fluoro-7-deazapurine.

In certain embodiments, lgRNAs comprise nucleotides modified in base moieties of crgRNA, and non-limiting examples include 2,6-diaminopurine, 5-fluorouracil, pseudouracil, and 7-fluoro-7-deazapurine.

In certain embodiments, lgRNAs comprise modified nucleotides in both crgRNAs and tracrgRNAs.

In certain embodiments, lgRNAs comprise nucleotides modified in both base moieties and sugar moieties.

In certain embodiments, the nNt-linker comprises a 1,4-disubstituted 1,2,3-triazole formed between an alkyne and an azide via [3+2] cycloaddition catalyzed by Cu(I) or without Cu(I) catalysis (such as strain-promoted azide-alkyne cycloaddition (SPAAC)).

In certain embodiments, the nNt-linker is a thioether by chemical ligation between a thiol and a maleimide, or other functional groups.

In some embodiments, the 3'-end nucleotide of crgRNA is a modified U or C, and the nNt-linker is attached at 5-position of the nucleoside base, or a 7-deazaguanine or 7-deazaadenine, and the nNt-linker is attached at 7-position of the nucleoside base, or a purine nucleotide, and the nNt-linker is attached at the 8-position of the nucleoside base.

In other embodiments is, and the nNt-linker is attached at the 2'- or 3'-position of the sugar moiety of the 3'-end nucleotide of crgRNA.

In some embodiments, the 5'-end nucleotide of tracrgRNA is a modified U or C, and the nNt-linker is attached at 5-position of the nucleoside base, or a 7-deazaguanine or 7-deazaadenine, and the nNt-linker is attached at 7-position of the nucleoside base, or a purine nucleotide, and the nNt-linker is attached at the 8-position of the nucleoside base.

In other embodiments, the nNt-linker is attached at the 2'- or 5'-position of the sugar moiety of the 5'-end nucleotide of tracrgRNA.

In some embodiments, the 5'-end nucleotide of tracrgRNA is base-paired with the 3'-end nucleotide of crgRNA as A . . . 0 or G . . . C.

In other embodiments, the 5'-end nucleotide of tracrgRNA and the 3'-end nucleotide of crgRNA are not base-paired.

In certain embodiments, lgRNAs comprise spacers in crgRNA selected from sequences of 12~20 nt of HIV genomes, of which each thymine is replaced with uracil, immediately before a PAM (such as NGG). The spacer RNA oligomers have the same sequences as the sense strands (5'→3') of the genomes, and namely are their RNA transcripts with or without further chemical modifications, or have the same sequences as the antisense strands (5'→3') of the genomes, and namely are their antisense RNA transcripts with or without further chemical modifications.

In certain embodiments, lgRNAs comprise spacers in crgRNA selected from sequences of 12~20 nt of HBV genomes, of which each thymine is replaced with uracil, immediately before a PAM (such as NGG). The spacer RNA oligomers have the same sequences as the sense strands (5'→3') of the genomes, and namely are their RNA transcripts with or without further chemical modifications, or have the same sequences as the antisense strands (5'→3') of the genomes, and namely are their antisense RNA transcripts with or without further chemical modifications.

In certain embodiments, lgRNAs comprise spacers in crgRNA selected from sequences of 12~20 nt of HSV genomes, of which each thymine is replaced with uracil, immediately before a PAM (such as NGG). The spacer RNA oligomers have the same sequences as the sense strands (5'→3') of the genomes, and namely their RNA transcripts with or without further chemical modifications, or have the same sequences as the antisense strands (5'→3') of the genomes, and namely are their antisense RNA transcripts with or without further chemical modifications.

In certain embodiments, lgRNAs comprise spacers in crgRNA selected from sequences of 12~20 nt of EBV genomes, of which each thymine is replaced with uracil, immediately before a PAM (such as NGG). The spacer RNA oligomers have the same sequences as the sense strands (5'→3') of the genomes, and namely their RNA transcripts with or without further chemical modifications, or have the same sequences as the antisense strands (5'→3') of the genomes, and namely are their antisense RNA transcripts with or without further chemical modifications.

In certain embodiments, lgRNAs are mixtures comprising lgRNA constructs with different spacers corresponding to different loci of viral genomes and/or variants of a single locus of target genomes. Useful selection methods to identify sequences having extremely low to no homology between the foreign viral genome and host cellular genome including endogenous retroviral DNA include bioinformatics screening to minimize and/or exclude off-target human transcriptome and essential untranslated genomic sites, and to optimize the efficacy of target cleavage.

DETAILED DESCRIPTION OF THE INVENTION

An aspect of the invention is directed to chemically ligated guide RNA oligonucleotides (lgRNA) comprising two functional RNA modules (crgRNA and tracrgRNA, crgRNA and dual-tracrgRNA or multiple-tracrgRNA) joined by chemical nNt-linkers, their complexes with CRISPR-Cas9, preparation methods of Cas9-lgRNA complexes and their uses in the treatments of viral infections in humans.

In some embodiments, this chemical ligation strategy provides diverse chemically modified lgRNAs for optimization for better efficacy in cleaving viral genomic DNAs.

In other embodiments, this chemical ligation strategy provides diverse chemically modified lgRNAs for minimizing off-target cleavages of host genomic DNAs with or without engineering Cas9 proteins.

In some embodiments, this chemical ligation strategy provides diverse chemically modified lgRNAs for decreasing the size of Cas9-lgRNA complex by engineering Cas9 proteins, or for full functional substitution of Cas9 with smaller natural/engineered CRISPR-associated proteins thus more amenable to delivery in human cells, for efficient administrations and better dosage forms.

In other embodiments, Cas9-lgRNA complexes are formulated with transfecting agents such as cationic lipids, cationic polymers and/or cell penetrating peptides for antiviral therapies, either alone or in combination with other direct-acting antiviral agents (DAA).

BRIEF DESCRIPTION OF THE DRAWINGS

FIG. 1: shows crRNA (Top, SEQ ID NO: 5)::tracrRNA (Bottom, SEQ ID NO: 6) complex in upper diagram, and schematic illustration of a Cas9/gRNA complex bound at its target DNA site at the bottom.

FIG. 2: shows molecular surface representation of the crystal structure of a Cas9/gRNA complex, and the tetraloop is free of any interactions with Cas9.

FIG. 3: shows a molecular model of lgRNA. The ligation nNt-linker (ligation1) is a triazole.

FIG. 4: shows a general procedure to prepare a Cas9-lgRNA complex.

DEFINITION

The definitions of terms used herein are consistent to those known to those of ordinary skill in the art, and in case of any differences the definitions are used as specified herein instead.

The term "nucleoside" as used herein refers to a molecule composed of a heterocyclic nitrogenous base, containing an N-glycosidic linkage with a sugar, particularly a pentose. An extended term of "nucleoside" as used herein also refers to acyclic nucleosides and carbocyclic nucleosides.

The term "nucleotide" as used herein refers to a molecule composed of a nucleoside monophosphate, di-, or triphosphate containing a phosphate ester at 5'-, 3'-position or both. The phosphate can also be a phosphonate.

The term of "oligonucleotide" (ON) is herein used interchangeably with "polynucleotide", "nucleotide sequence", and "nucleic acid", and refers to a polymeric form of nucleotides of any length, either deoxyribonucleotides or ribonucleotides, or analogs thereof. An oligonucleotide may comprise one or more modified nucleotides, which may be imparted before or after assembly of such as oligonucleotide. The sequence of nucleotides may be interrupted by non-nucleotide components.

The term of "crispr/cas9" refers to the type II CRISPR-Cas system from *Streptococcus pyogenes*. The type II CRISPR-Cas system comprises protein Cas9 and two non-coding RNAs (crRNA and tracrRNA). These two noncoding RNAs were further fused into one single guide RNA (sgRNA). The Cas9/sgRNA complex binds double-stranded DNA sequences that contain a sequence match to the first 17-20 nucleotides of the sgRNA and immediately before a protospacer adjacent motif (PAM). Once bound, two independent nuclease domains (HNH and RuvC) in Cas9 each cleaves one of the DNA strands 3 bases upstream of the PAM, leaving a blunt end DNA double stranded break (DSB).

The term of "off-target effects" refers to non-targeted cleavage of the genomic DNA target sequence by Cas9 in spite of imperfect matches between the gRNA sequence and the genomic DNA target sequence. Single mismatches of the gRNA can be permissive for off-target cleavage by Cas9. Off-target effects were reported for all the following cases: (a) same length but with 1-5 base mismatches; (b) off-target site in target genomic DNA has one or more bases missing ('deletions'); (c) off-target site in target genomic DNA has one or more extra bases ('insertions').

The term of "guide RNA" (gRNA) refers to a synthetic fusion of crRNA and tracrRNA via a tetraloop (GAAA) (defined as sgRNA) or other chemical linkers such as an nNt-Linker (defined as lgRNA), and is used interchangeably with "chimeric RNA", "chimeric guide RNA", "single guide RNA" and "synthetic guide RNA". The gRNA contains secondary structures of the repeat:anti-repeat duplex, stem loops 1-3, and the linker between stem loops 1 and 2.

The term of "dual RNA" refers to hybridized complex of the short CRISPR RNAs (crRNA) and the trans-activating crRNA (tracrRNA). The crRNA hybridizes with the tracrRNA to form a crRNA:tracrRNA duplex, which is loaded onto Cas9 to direct the cleavage of cognate DNA sequences bearing appropriate protospacer-adjacent motifs (PAM).

The term of "lgRNA" refers to guide RNA (gRNA) joined by chemical ligations to form non-nucleotide linkers (nNt-linkers) between crgRNA and tracrgRNA, or at other sites.

The terms of "dual lgRNA", "triple lgRNA" and "multiple lgRNA" refer to hybridized complexes of the synthetic guide RNA fused by chemical ligations via non-nucleotide linkers. Dual tracrgRNA is formed by chemical ligation between tracrgRNA1 and tracrgRNA2 (RNA segments of 30 nt), and crgRNA (~30 nt) is fused with a dual tracrgRNA to form a triple lgRNA duplex, which is loaded onto Cas9 to direct the cleavage of cognate DNA sequences bearing appropriate protospacer-adjacent motifs (PAM). Each RNA segment can be readily accessible by chemical manufacturing and compatible to extensive chemical modifications.

The term "guide sequence" refers to the about 20 bp sequence within the guide RNA that specifies the target site and is herein used interchangeably with the terms "guide" or "spacer". The term "tracr mate sequence" may also be used interchangeably with the term "direct repeat(s)".

The term of "crgRNA" refers to crRNA equipped with chemical functions for conjugation/ligation and is used interchangeably with crRNA in an lgRNA comprising at least one non-Nucleotide linker. The oligonucleotide may be chemically modified close to its 3'-end, any one or several nucleotides, or for its full sequence.

The term of "tracrgRNA" refers to tracrRNA equipped with chemical functions for conjugation/ligation and is used interchangeably with tracrRNA in an lgRNA comprising at least one non-Nucleotide linker. The oligonucleotide may be chemically modified at any one or several nucleotides, or for its full sequence.

The term of "the protospacer adjacent motif (PAM)" refers to a DNA sequence immediately following the DNA sequence targeted by Cas9 in the CRISPR bacterial adaptive immune system, including NGG, NNNNGATT, NNAGAA, NAAAC, and others from different bacterial species where N is any nucleotide.

The term of "chemical ligation" refers to joining together synthetic oligonucleotides via an nNt-linker by chemical methods such as click ligation (the azide-alkyne reaction to produce a triazole linkage), thiol-maleimide reaction, and formations of other chemical groups.

The term of "complementary" refers to the ability of a nucleic acid to form hydrogen bond(s) with another nucleic acid sequence by either traditional Watson-Crick or other non-traditional types. Cas9 contains two nuclease domains, HNH and RuvC, which cleave the DNA strands that are complementary and noncomplementary to the 20 nucleotide (nt) guide sequence in crRNAs, respectively.

The term of "Hybridization" refers to a reaction in which one or more polynucleotides form a complex that is stabilized via hydrogen bonding between the bases of the nucleotide residues. The complex may comprise two strands forming a duplex structure, three or more strands forming a multi stranded complex, a single self-hybridizing strand, or any combination of these. A sequence capable of hybridizing with a given sequence is referred to as the "complement" of the given sequence.

The synonymous terms "hydroxyl protecting group" and "alcohol-protecting group" as used herein refer to substituents attached to the oxygen of an alcohol group commonly employed to block or protect the alcohol functionality while reacting other functional groups on the compound. Examples of such alcohol-protecting groups include but are not limited to the 2-tetrahydropyranyl group, 2-(bisacetoxyethoxy)methyl group, trityl group, trichloroacetyl group, carbonate-type blocking groups such as benzyloxycarbonyl, trialkylsilyl groups, examples of such being trimethylsilyl, tert-butyldimethylsilyl, tert-butyldiphenylsilyl, phenyldimethylsilyl, triiospropylsilyl and thexyldimethylsilyl, ester groups, examples of such being formyl, ($C_1$-$C_{10}$) alkanoyl optionally mono-, di- or tri-substituted with ($C_1$-$C_6$) alkyl, ($C_1$-$C_6$) alkoxy, halo, aryl, aryloxy or haloaryloxy, the aroyl group including optionally mono-, di- or tri-substituted on the ring carbons with halo, ($C_1$-$C_6$) alkyl, ($C_1$-$C_6$) alkoxy wherein aryl is phenyl, 2-furyl, carbonates, sulfonates, and ethers such as benzyl, p-methoxybenzyl, methoxymethyl, 2-ethoxyethyl group, etc. The choice of alcohol-protecting group employed is not critical so long as the derivatized alcohol group is stable to the conditions of subsequent reaction(s) on other positions of the compound of the formula and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and G. M. Wuts, T. W. Greene, "Protective Groups in Organic Synthesis", John Wiley & Sons Inc., Hoboken, N.J., 2007, which are hereby incorporated by reference. The related terms "protected hydroxyl" or "protected alcohol" define a hydroxyl group substituted with a hydroxyl protecting group as discussed above.

The term "nitrogen protecting group," as used herein, refers to groups known in the art that are readily introduced on to and removed from a nitrogen atom. Examples of nitrogen protecting groups include but are not limited to acetyl (Ac), trifluoroacetyl, Boc, Cbz, benzoyl (Bz), N,N-dimethylformamidine (DMF), trityl, and benzyl (Bn). See also G. M. Wuts, T. W. Greene, "Protective Groups in Organic Synthesis", John Wiley & Sons Inc., Hoboken, N.J., 2007, and related publications.

The term of "Isotopically enriched" refers to a compound containing at least one atom having an isotopic composition other than the natural isotopic composition of that atom. The term of "Isotopic composition" refers to the amount of each isotope present for a given atom, and "natural isotopic composition" refers to the naturally occurring isotopic composition or abundance for a given atom. As used herein, an isotopically enriched compound optionally contains deuterium, carbon-13, nitrogen-15, and/or oxygen-18 at amounts other than their natural isotopic compositions.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent known to be useful for, or which has been or is currently being used for the treatment or prevention of a disorder or one or more symptoms thereof.

Nucleotides

In some embodiments, the crRNA and tracrRNA are truncated at 3'-end and 5'-end, respectively:

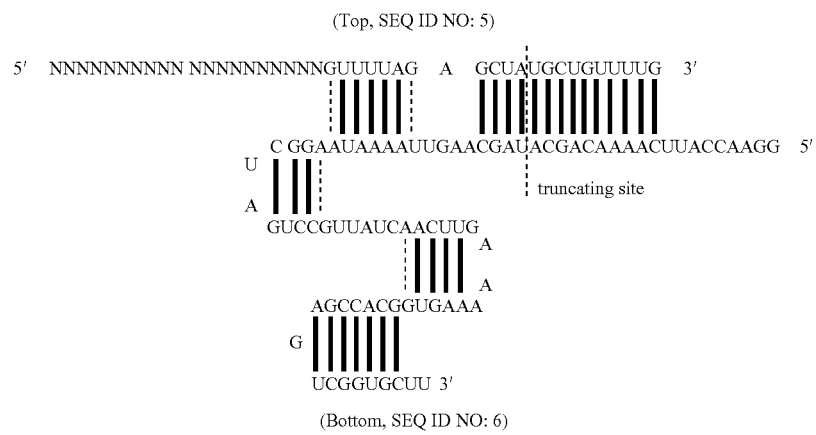

and the duplex end is replaced with a small molecule non-nucleotide linker (nNt-linker, ligation1), instead of the tetraloop (GAAA) in sgRNA, to form a ligated dual lgRNA:

wherein "NNNNNNNNNN NNNNNNNNNN" is a guide sequence of 17-20 nt, and N is preferably a ribonucleotide with intact 2'-OH, and wherein ")" is a chemical nNt-linker.

In other embodiments, tracrgRNA is a ligated dual oligonucleotide (via ligation2, the inner ligation between tracrgRNA1 and tracrgRNA2), or a multiple oligonucleotide. Non-limiting examples include:

(SEQ ID NO: 7)

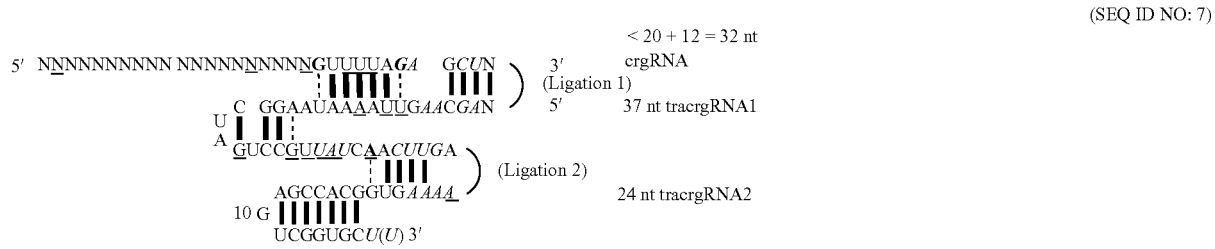

(SEQ ID NO: 8)

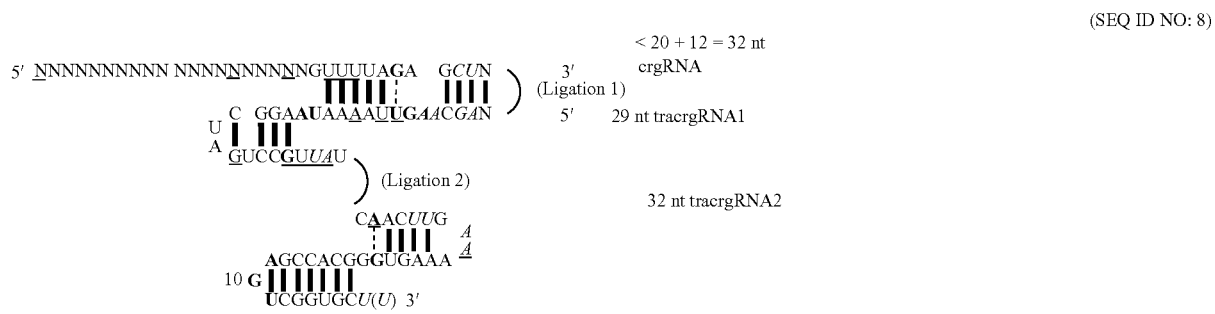

(SEQ ID NO: 9)

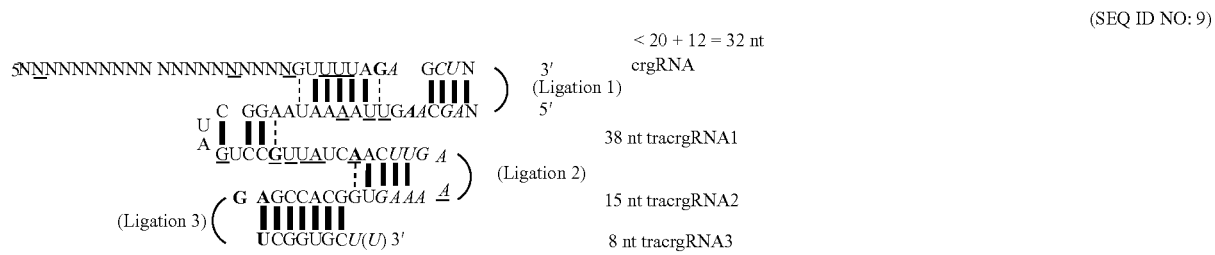

In some embodiments, the crRNA and tracrRNA are further truncated, and non-limiting examples of resulting lgRNAs include:

(SEQ ID NO: 10)

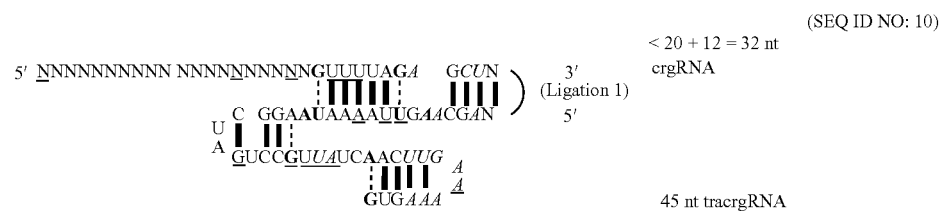

(SEQ ID NO: 11)

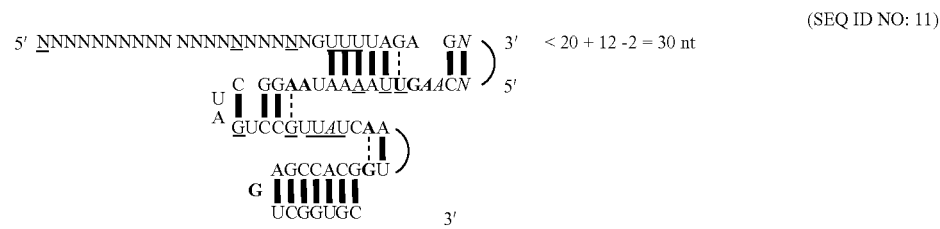

-continued

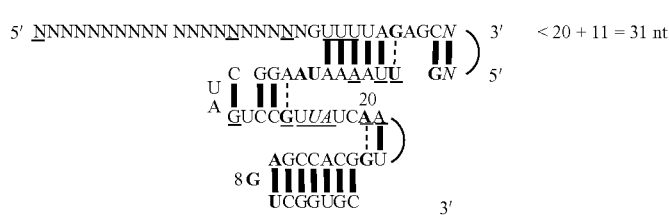
(SEQ ID NO: 12)
< 20 + 11 = 31 nt

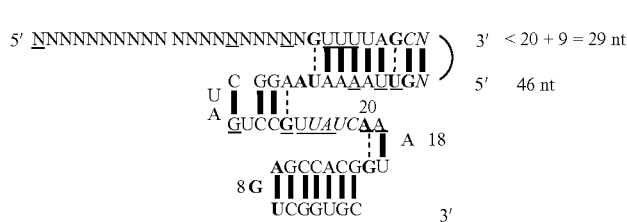
(SEQ ID NO: 13)
< 20 + 9 = 29 nt
46 nt

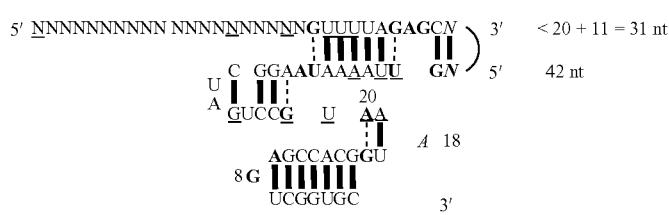
(SEQ ID NO: 14)
< 20 + 11 = 31 nt
42 nt

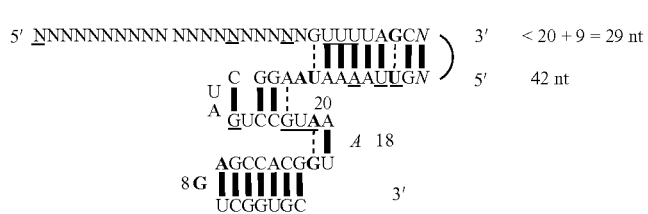
(SEQ ID NO: 15)
< 20 + 9 = 29 nt
42 nt

The two RNA modules (crgRNA and tracrgRNA, crgRNA and dual-tracrgRNA or multiple-tracrgRNA) are synthesized chemically by phosphoramidite chemistry and ligation chemistry either on solid support(s) or in solution. Non-limiting examples of compounds (oligonucleotide azides, oligonucleotide alkynes, oligonucleotide thiols, and oligonucleotide maleimides) and synthetic methods include:

1. Ligation Via Formation of a 1,2,3-Triazole Cross-Linker a. Direct modification of fully deprotected oligonucleotide amine (such as ON-1) provides RNA alkynes or azides (ON-2):

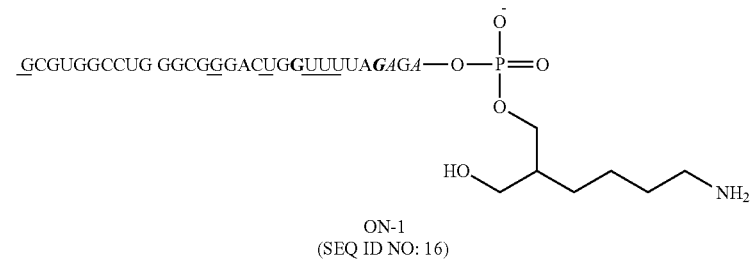
ON-1
(SEQ ID NO: 16)

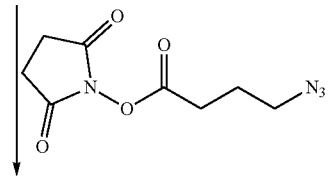

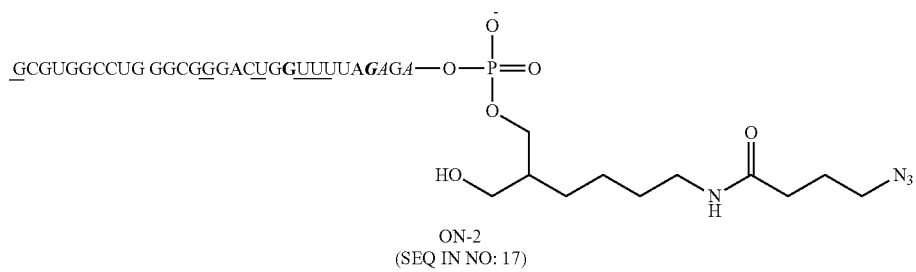
ON-2
(SEQ IN NO: 17)
Non-limiting examples of crosslinking reagents include:
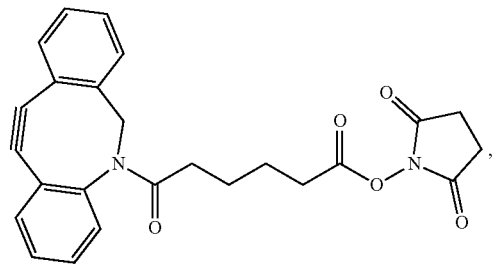
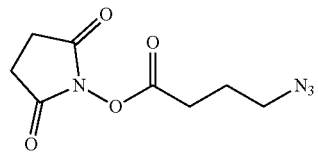
b. Azide and alkyne functions are introduced as phosphoramidites in chemical synthesis of the RNAs (ON-5 and ON-7):
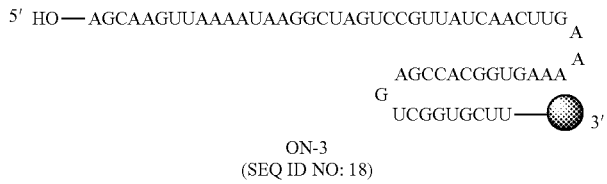
ON-3
(SEQ ID NO: 18)
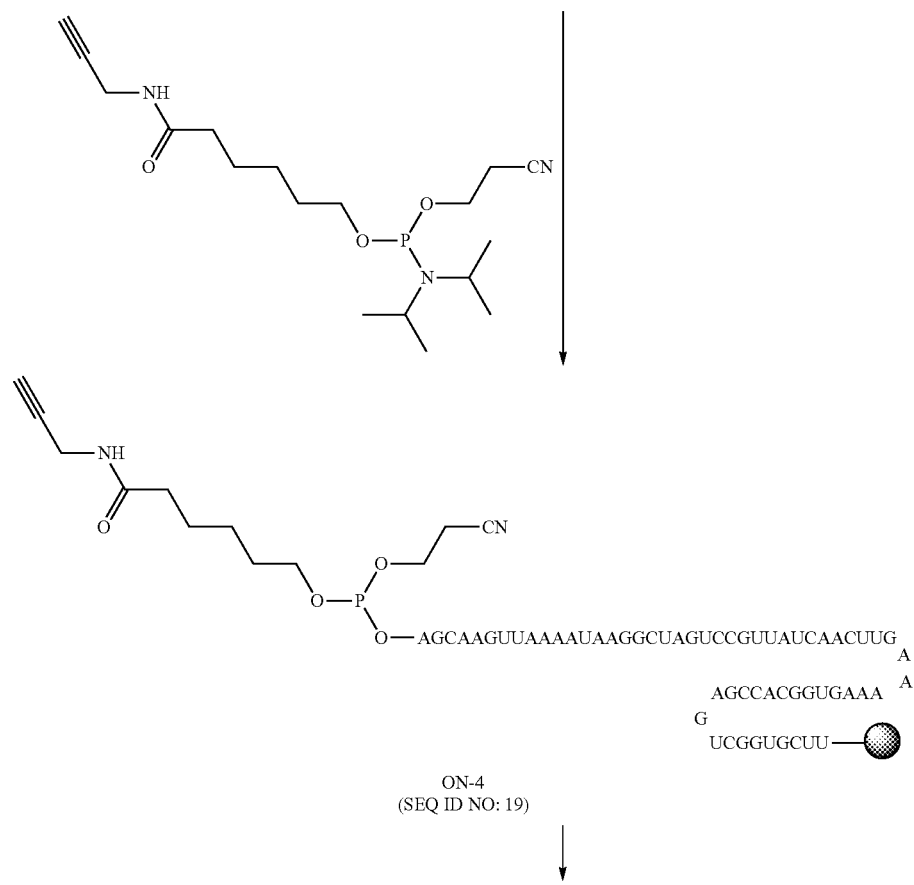
ON-4
(SEQ ID NO: 19)

-continued
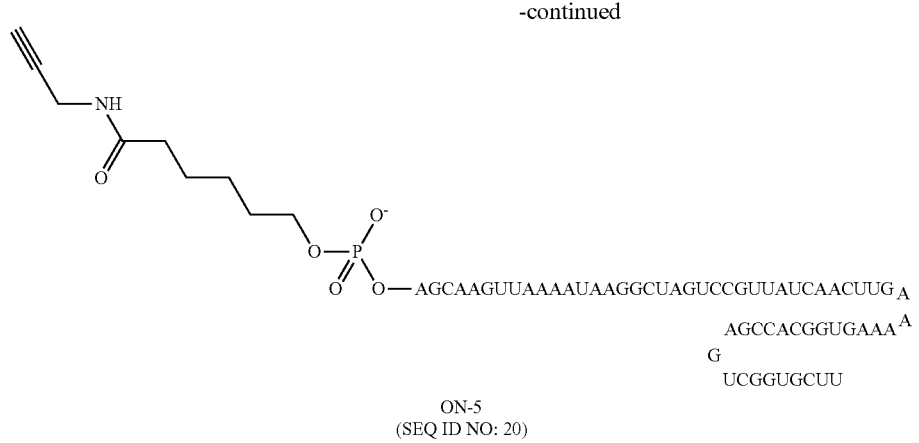
ON-5
(SEQ ID NO: 20)
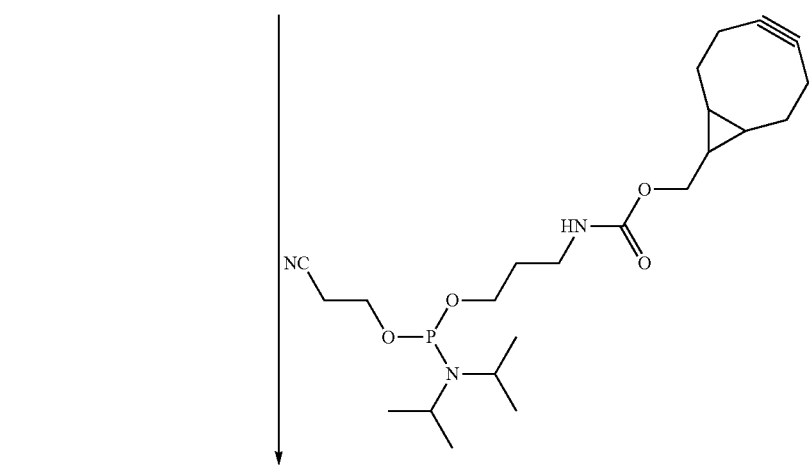
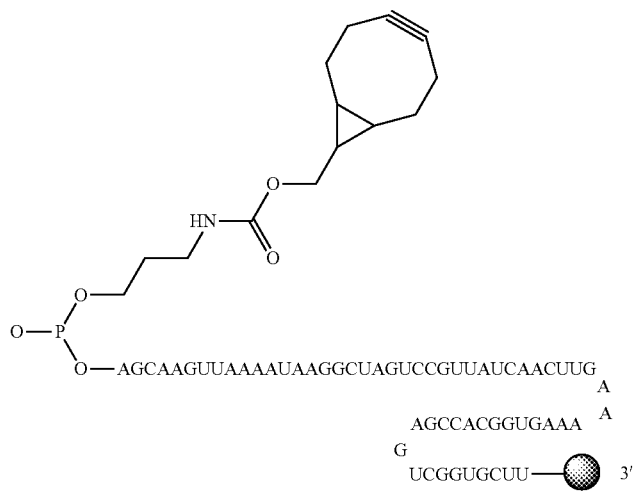
ON-6
(SEQ ID NO: 21)

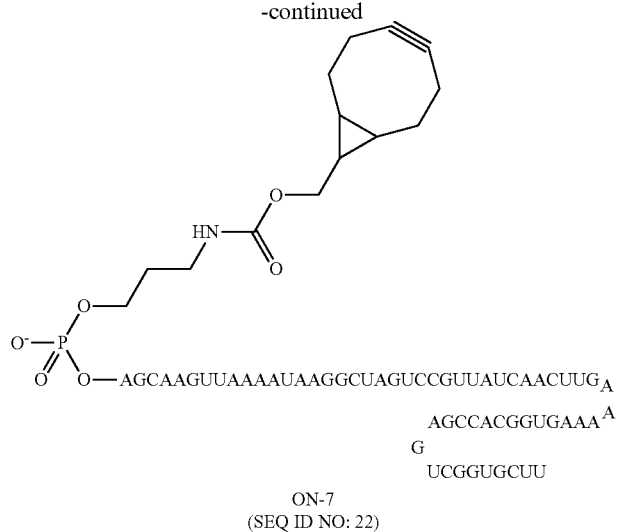
ON-7
(SEQ ID NO: 22)
Non-limiting examples of these phosphoramidites include:
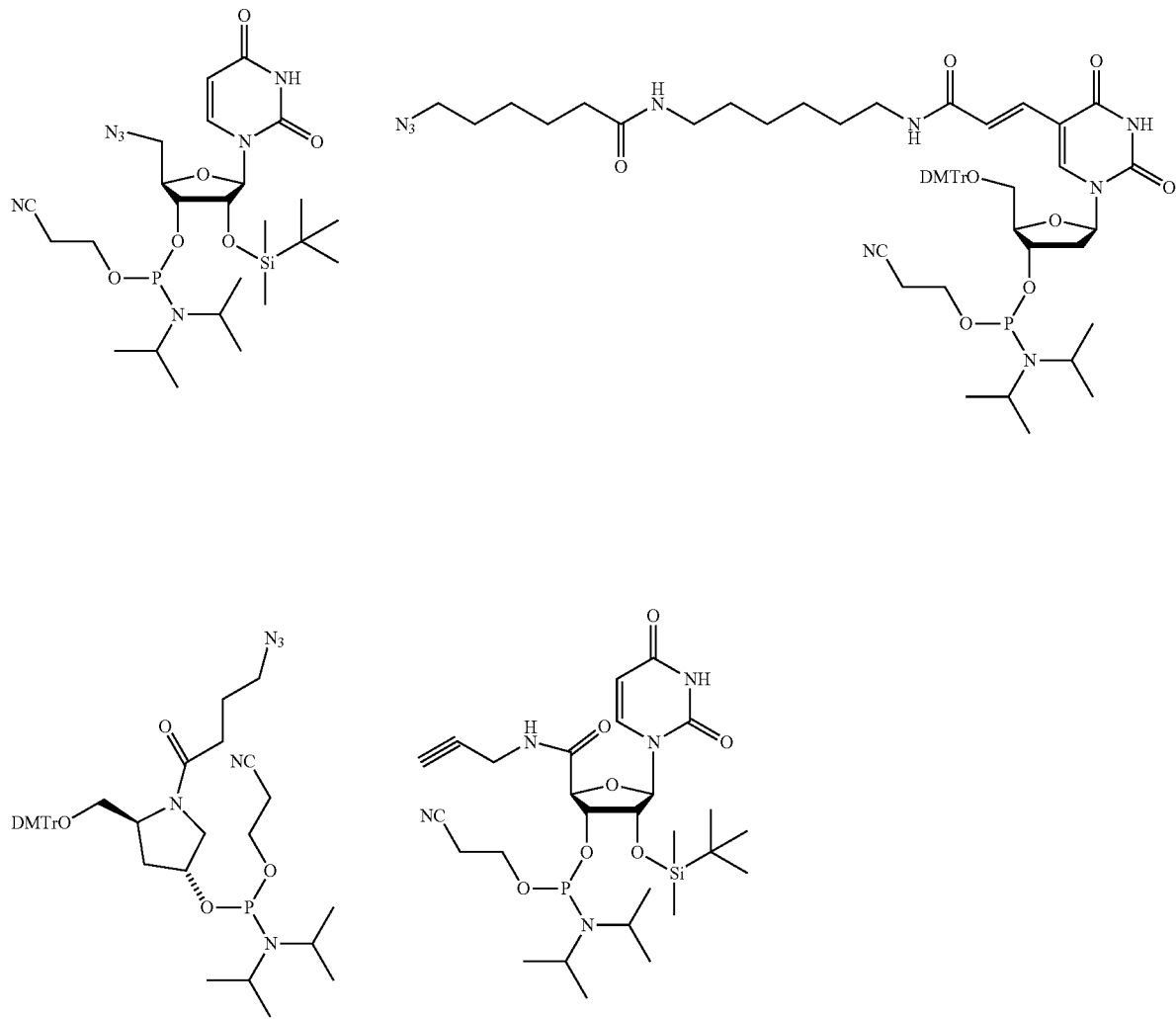

27 28
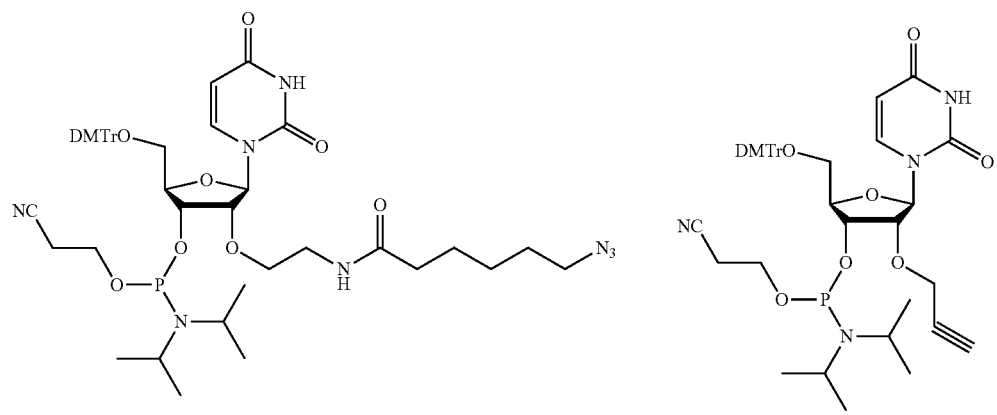
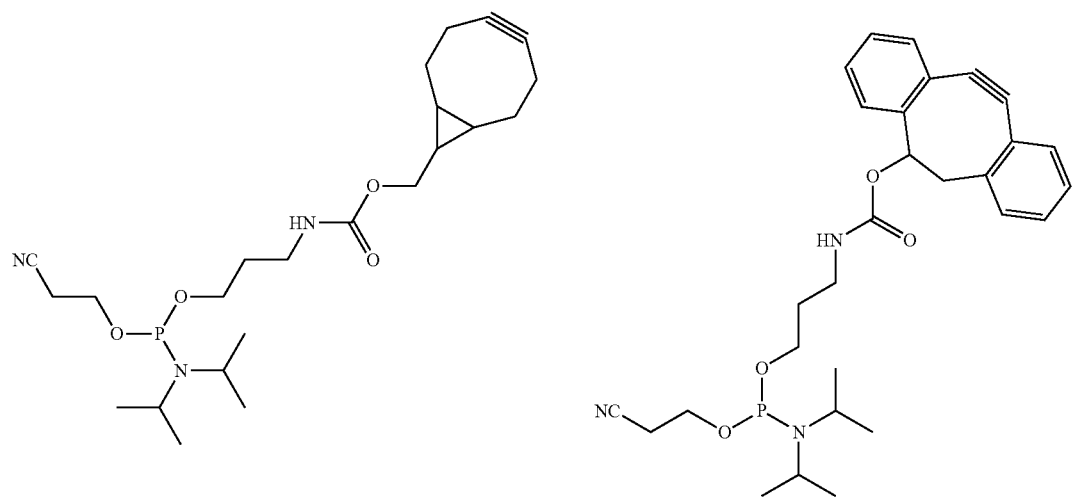
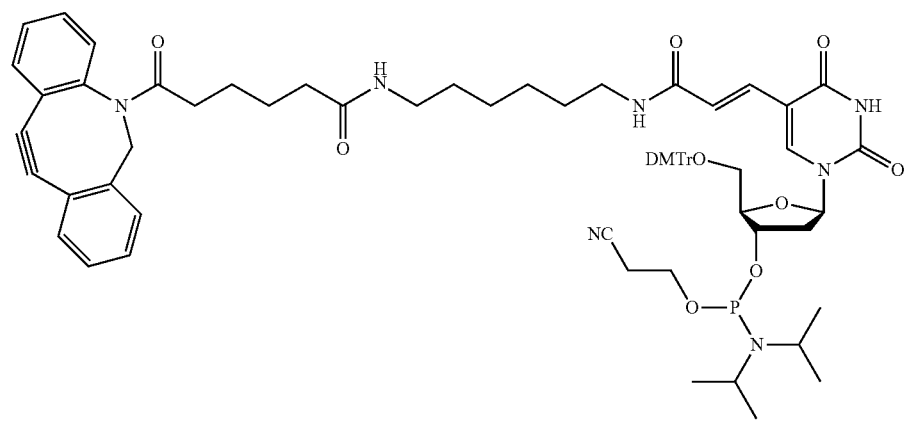

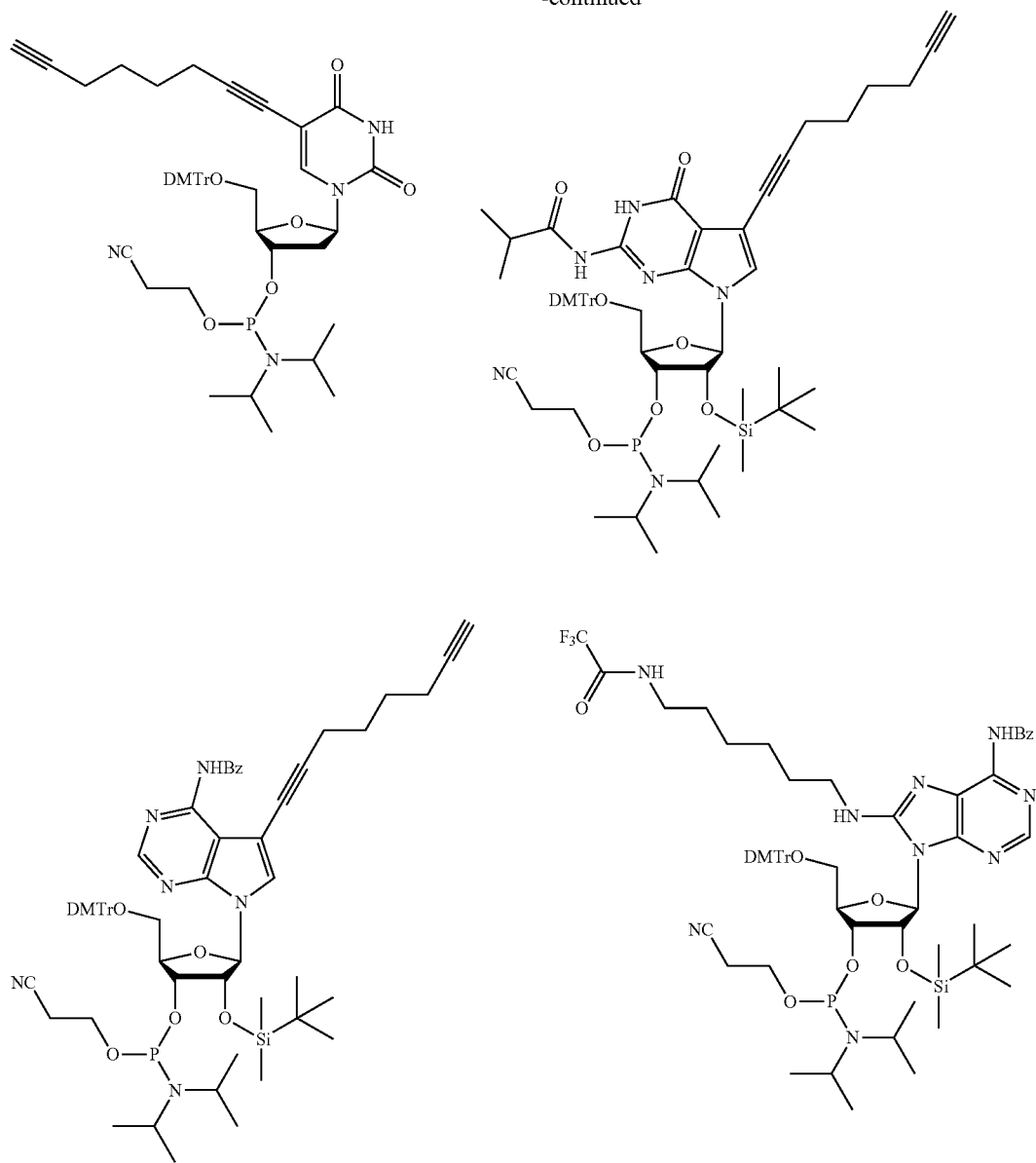
c. Preparation of lgRNA by chemical ligation via click chemistry of crgRNA and tracrgRNA and annealing to form RNA duplex, or by annealing followed by chemical ligation via click chemistry.
2. Ligation Via Formation of a Thioether Cross-Linker
a. Thiol function is introduced as a phosphoramidite in chemical synthesis of the RNAs:
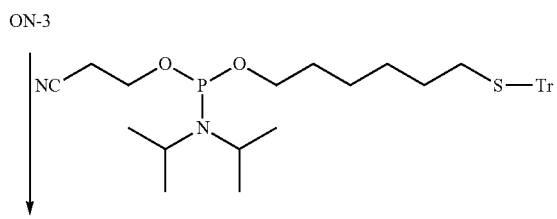
ON-3

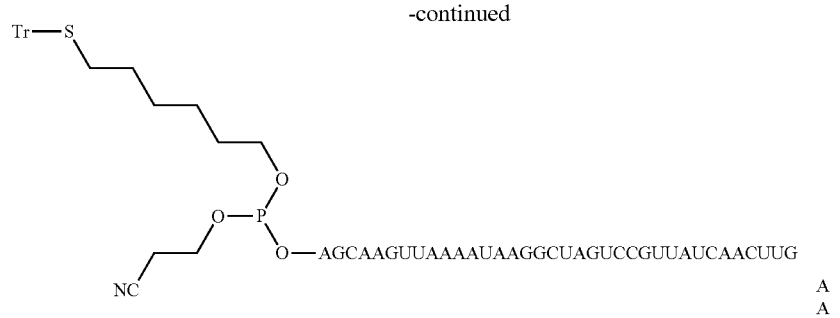
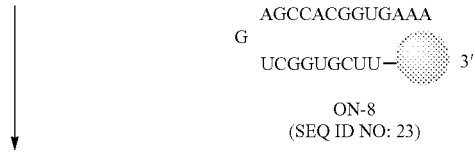
ON-8
(SEQ ID NO: 23)
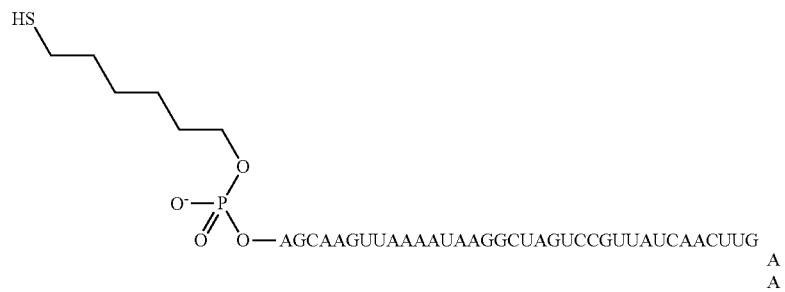
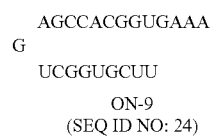
ON-9
(SEQ ID NO: 24)
Non-limiting examples of these phosphoramidites include:
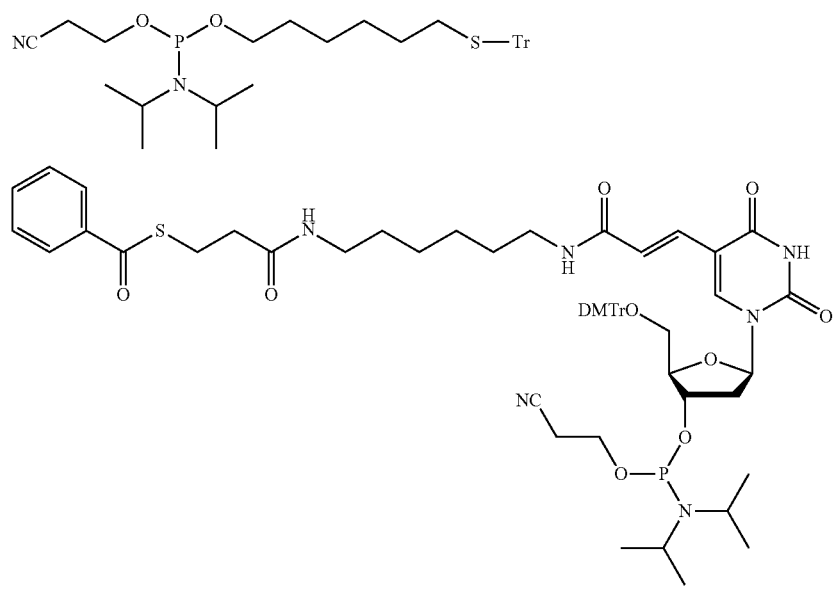

-continued
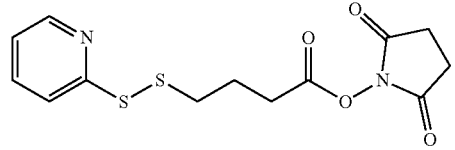
SPDB
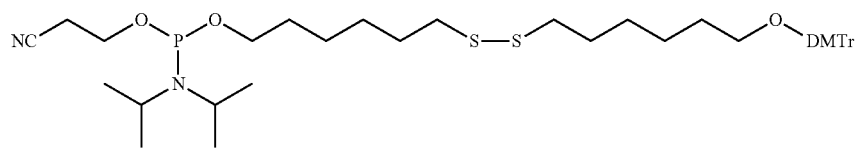
b. Direct modification of fully deprotected oligonucleotide amine (such as ON-1) provides the RNA maleimide (ON-10):
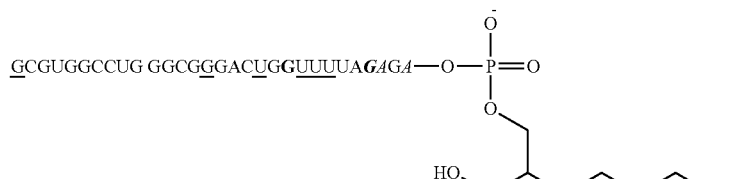
ON-1
(SEQ ID NO: 16)
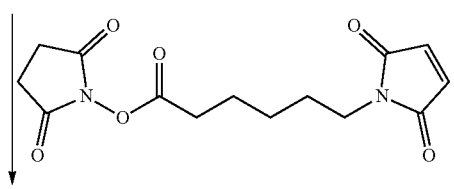
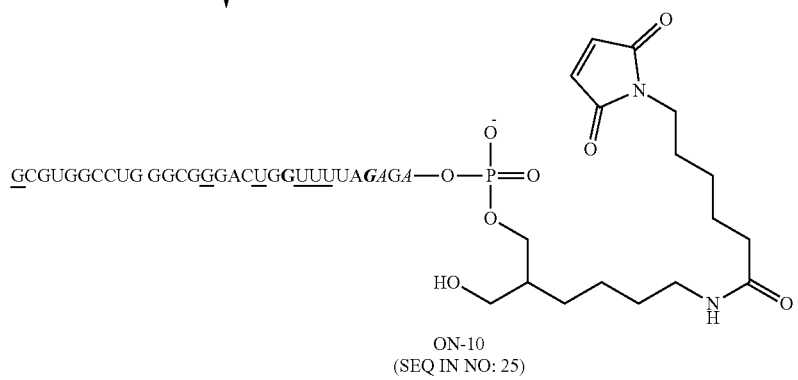
ON-10
(SEQ IN NO: 25)
Non-limiting examples of maleimide crosslinking reagents include:
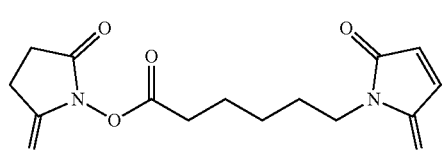
EMCS
-continued
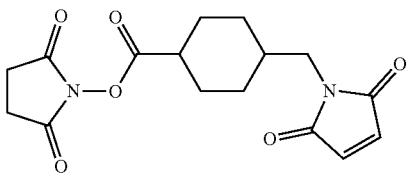
SMCC

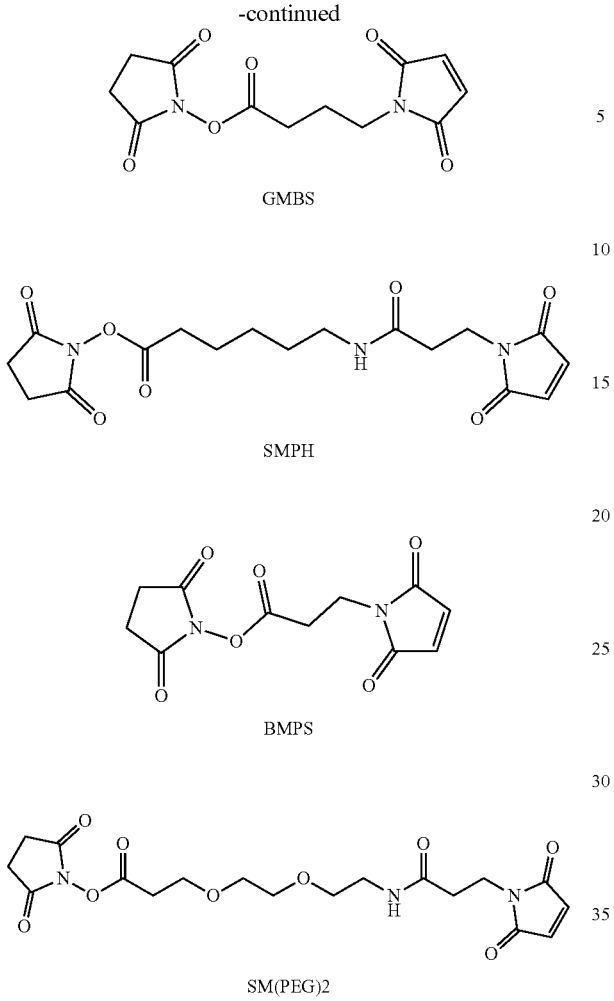

GMBS

SMPH

BMPS

SM(PEG)2 c. Preparation of lgRNA by chemical ligation via thio-ether formation between crgRNA and tracrgRNA and annealing to form RNA duplex, or by annealing followed by chemical ligation via thio-ether formation.

The above chemical ligations for ligation between crgRNA and tracrgRNA (ligation1) are applicable to formation of ligated dual tracrgRNA between tracrgRNA1 and tracrgRNA2 (ligation2).

In some embodiments, the two ligations (ligation1 and ligation2) are chemically orthogonal. Non-limiting examples include:

a. ligation2 by a triazole linker and ligation1 by a thio-ether linker;

b. ligation2 by a thioether linker and ligation1 by a triazole linker;

c. ligation2 by some linker and ligation1 by a second linker, which is chemically orthogonal to that for ligation2;

In other embodiments, the two ligations can be formed by the same chemistry such as an azide-alkyne [3+2] cycloaddition.

An aspect of the invention is directed to CRISPR-Cas9-lgRNA system:

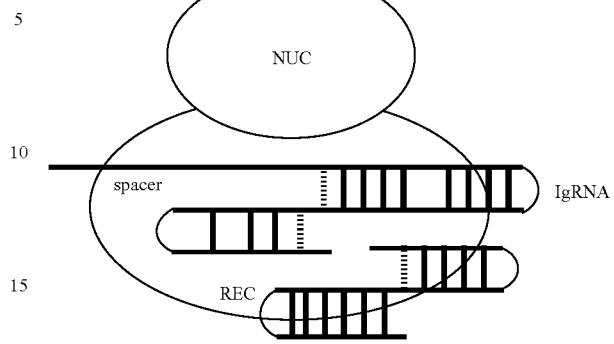

II wherein lgRNA is a single ligated RNA composed of dual-modules, a triple or a multiple ligated RNA composed of dual-modules, and ligation sites are preferably located at tetraloop (A32-U37), and/or stem 2 (C70-G79) (of reported sgRNA designed for S. pyogenes Cas9), while any 3',5'-phosphodiester of sgRNA can be replaced by single nNt-Linker as a ligation site; and wherein Cas9 composed of a nuclease lobe (NUC) and a recognition lobe (REC) can be a CRISPR-associated protein other than the example of S. pyogenes Cas9 represented here, and can be any engineered Cas9.

Some aspects of the invention are directed to CRISPR-Cas9-lgRNA-transfecting reagent(s) systems.

Some aspects of the invention are directed to the use of CRISPR-Cas9-lgRNA system for antiviral therapy targeting against proviral DNAs or episomal circular DNAs.

In some embodiments, non-limiting examples of targeted viral genomic sequences of HBV include:

```
                                        (SEQ ID NO 36)
ctctgctagatcccagagtg [aGG], (SEQ ID NO 37)
gctatcgctggatgtgtctg [cGG], (SEQ ID NO 38)
tggacttctctcaatttct [a[G]G]G]G]], (SEQ ID NO 39)
gggggatcacccgtgtgtct [tGG], (SEQ ID NO 40)
tatgtggatgatgtggtactgg [gGG], (SEQ ID NO 41)
cctcaccatacagcactc [gGG], (SEQ ID NO 42)
gtgttggggtgagttgatgaatc [tGG],
``` wherein nucleotides in [ ] are PAMs, or any sequence of 17-20 nt upstream adjacent to a PAM sequence. More examples of such sequences can be found in literature (Lee, et al., WO2016/197132A1). A complete list of such sequences can be found in viral genomic sequences of HBV using online Basic Local Alignment Search Tool (BLAST). Useful selection methods to identify sequences having extremely low to no homology between the foreign viral genome and host cellular genome including endogenous retroviral DNA include bioinformatics screening to minimize and/or exclude off-target human transcriptome and essential untranslated genomic sites, and to optimize the efficacy of target cleavage.

In some embodiments, the therapeutic Cas9-lgRNAs comprise multiple lgRNAs targeting at different sites in viral genome (multiplex editing).

In some embodiments, multiple crgRNAs, including but not limited to sequences of YMDD and its mutations at catalytic domain of HBV polymerase, corresponding to

```
                              (SEQ ID NO 43)
tatgtggatgat gtggtactgg [gGG], (SEQ ID NO 44)
tatatggatgat gtggtattgg [gGG], (SEQ ID NO 45)
tatgtggatgat gtggtattgg [gGG], (SEQ ID NO 46)
tatatagatgat gtggtactgg [gGG],
``` are ligated to tracrgRNA to result in a mixture of lgRNAs, and thus of Cas9-lgRNAs to target drug resistance in therapies based on direct-acting antiviral agents (DAA).

In some embodiments, non-limiting examples of targeted viral genomic sequences of HW include:

```
                              (SEQ ID NO 47)
gattggcaga actacacacc [aGG], (SEQ ID NO 48)
atcagatatc cactgacctt [tGG], (SEQ ID NO 49)
gcgtggcctg ggcgggactg [gGG], (SEQ ID NO 50)
cagcagttct tgaagtactc [cGG],
``` wherein nucleotides in [ ] are PAMs, or any sequence of 17-20 nt upstream adjacent to a PAM sequence. A complete list of such sequences can be found in viral genomic sequences of HIV using online Basic Local Alignment Search Tool (BLAST). Useful selection methods to identify sequences having extremely low to no homology between the foreign viral genome and host cellular genome including endogenous retroviral DNA include bioinformatics screening to minimize and/or exclude off-target human transcriptome and essential untranslated genomic sites, and to optimize the efficacy of target cleavage.

In some embodiments, non-limiting examples of targeted viral genomic sequences of herpesviridae virus such as HSV and EBV include:

```
                              (SEQ ID NO 51)
gccctggaccaacccggccc [gGG], (SEQ ID NO 52)
ggccgctgccccgctccggg [tGG], (SEQ ID NO 53)
ggaagacaatgtgccgcca [tGG], (SEQ ID NO 54)
tctggaccagaaggctccgg [cGG], (SEQ ID NO 55)
gctgccgcggagggtgatga [cGG], (SEQ ID NO 56)
ggtggcccaccgggtccgct [gGG], (SEQ ID NO 57)
gtcctcgagggggccgtcgc [gGG],
``` wherein nucleotides in [ ] are PAMs, or any sequence of 17-20 nt upstream adjacent to a PAM sequence. The herpesvirus can be e.g., herpes simplex virus-1 (HSV-1), herpes simplex virus-2 (HSV-2), varicella zoster virus, Epstein-Barr virus, cytomegalovirus, human herpesvirus 6, human herpesvirus 7, or Kaposi's sarcoma-associated herpesvirus. A complete list of such sequences can be found in viral genomic sequences of herpesviridae virus using online Basic Local Alignment Search Tool (BLAST). Useful selection methods to identify sequences having extremely low to no homology between the foreign viral genome and host cellular genome including endogenous retroviral DNA include bioinformatics screening to minimize and/or exclude off-target human transcriptome and essential untranslated genomic sites, and to optimize the efficacy of target cleavage.

Other aspects of the invention are directed to the use of CRISPR-Cas9-lgRNA systems for gene edition and therapy.

Process for Preparations of Nucleotides

Other embodiments of this invention represent processes for preparation of these compounds provided herein, which can also be prepared by any other methods apparent to those skilled in the art.

Chemical Ligations

In some embodiments, the ligation between crgRNA and tracrgRNA (ligation1) is formation of triazole by Cu(I) catalyzed [2+3] cycloaddition. An azide or alkyne function is introduced at 3'-end of crgRNA which is an aminoalkyl oligonucleotide as represented by a non-limiting example of ON-11:

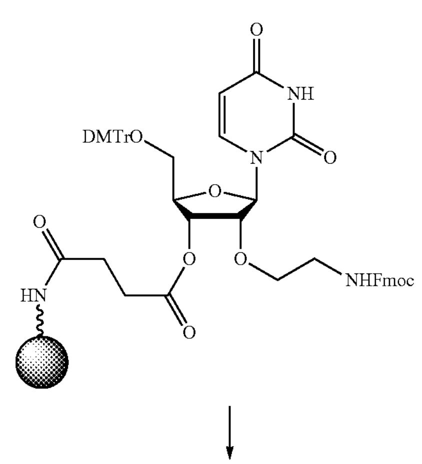

-continued
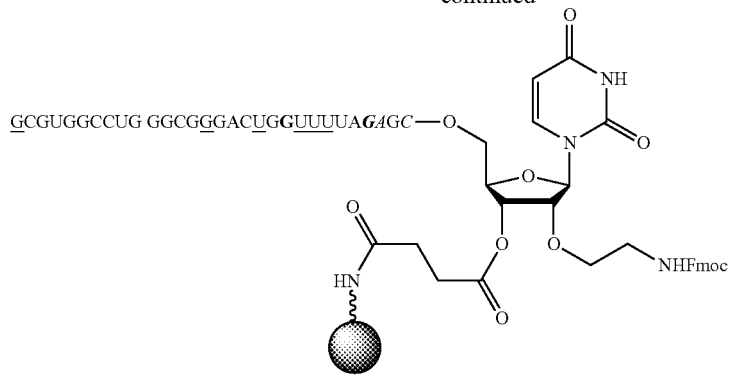
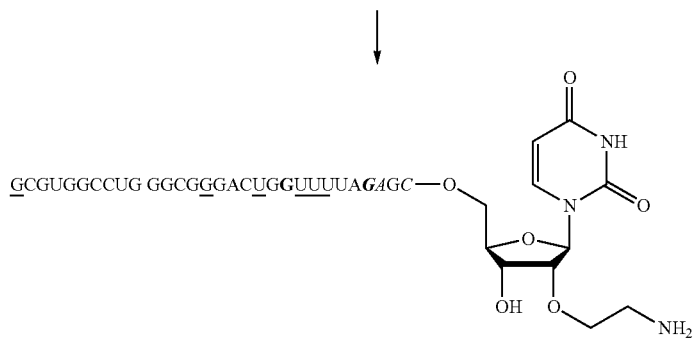
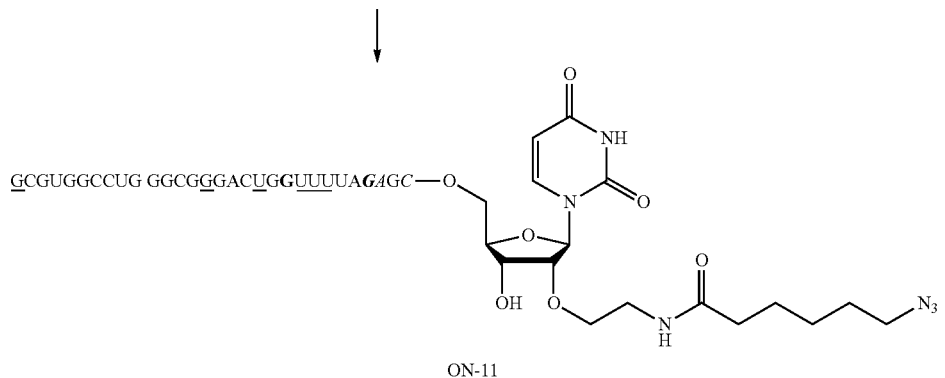
ON-11
(SEQ ID NO: 26)
An azide or alkyne function is introduced at 5'-end nucleotide of tracrgRNA as represented by a non-limiting example of ON-12 by solid phase supported synthesis:

41
-continued
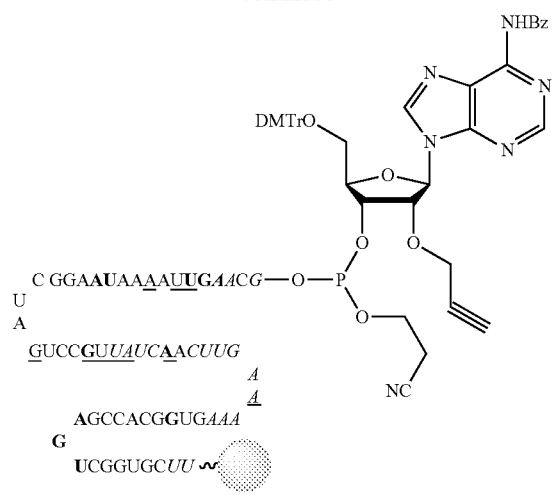
42
-continued
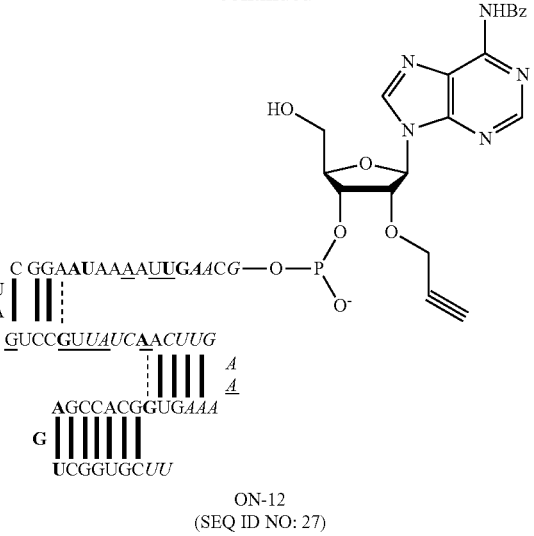
ON-12
(SEQ ID NO: 27)
TracrgRNA and crgRNA are then ligated by click reaction, and annealed as represented by a non-limiting example of ON-13:
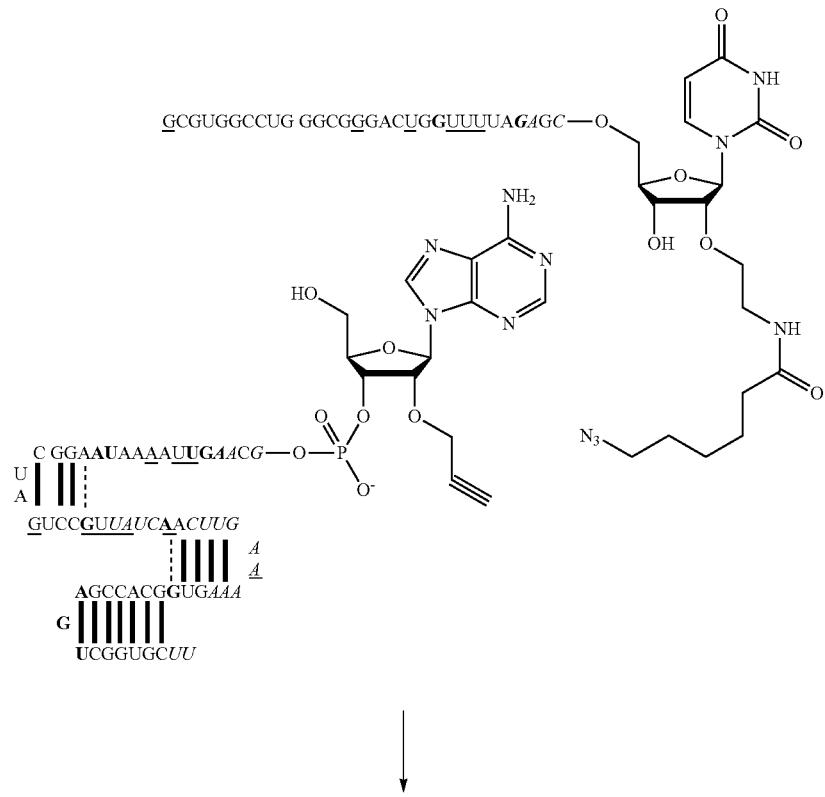

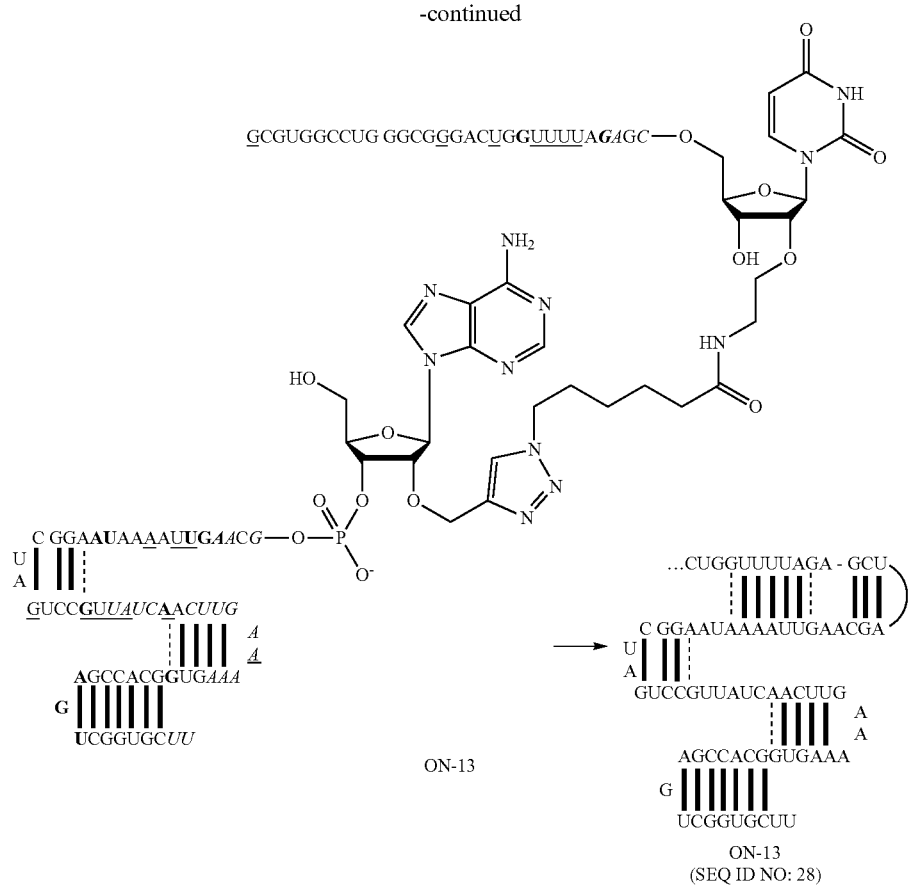

ON-13

ON-13
(SEQ ID NO: 28)

or are annealed, and then ligated by click chemistry.

In other embodiments, the ligation between crgRNA and tracrgRNA is formation of thioether linker or any compatible crosslinking chemistry.

In some embodiments for triple lgRNAs, the ligation in tracrgRNA (ligation2) and the ligation between crgRNA and tracrgRNA (ligation1) are orthogonal, and two ligations are realized in one pot:

A maleimide is introduced to 3'-end of crgRNA in solid phase supported synthesis as represented by a non-limiting example of ON-14:

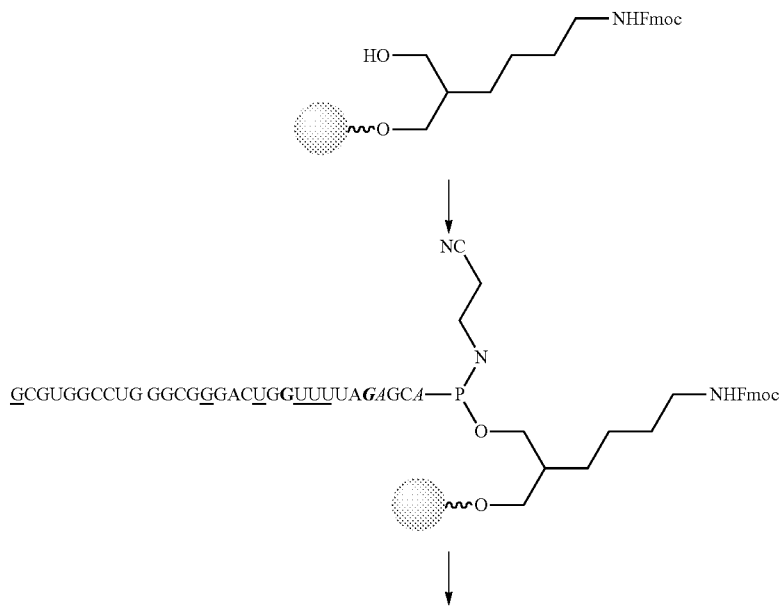

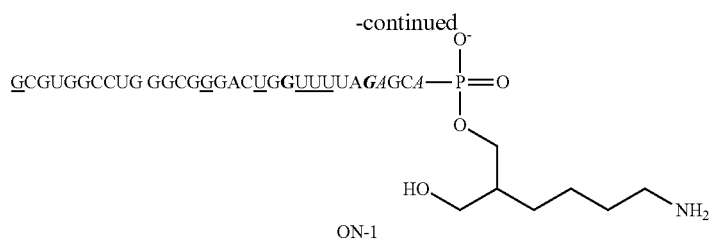
ON-1
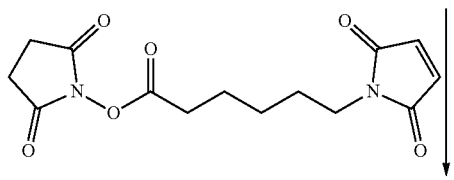
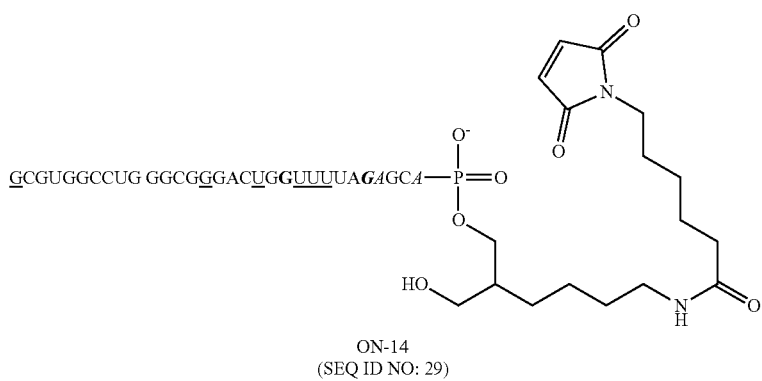
ON-14
(SEQ ID NO: 29)
A thiol and an azide are introduced at 5'-end and 3'-end of tracrgRNA1, respectively as represented by a non-limiting example of ON-15:
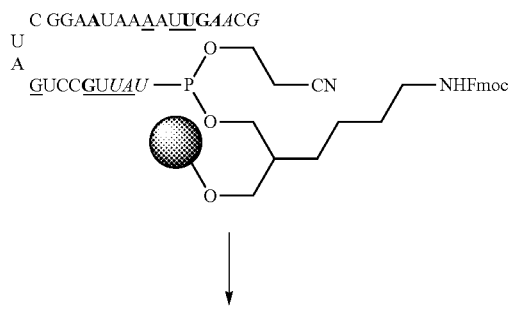

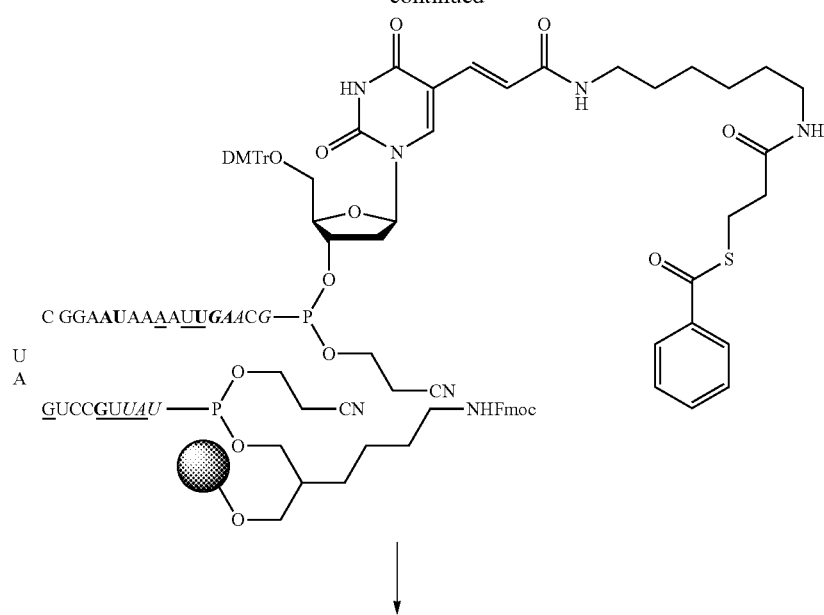
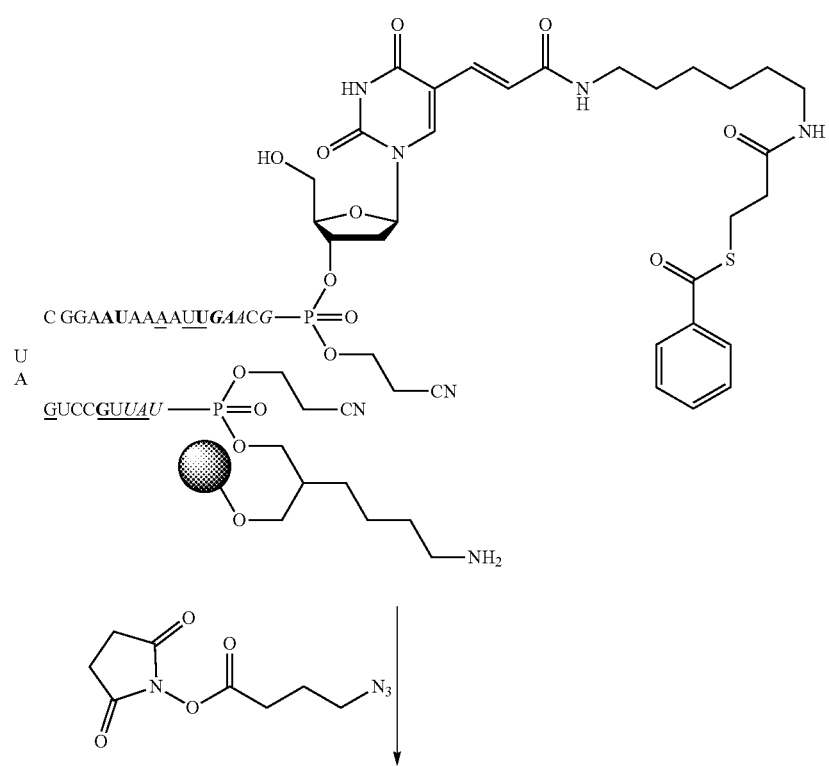

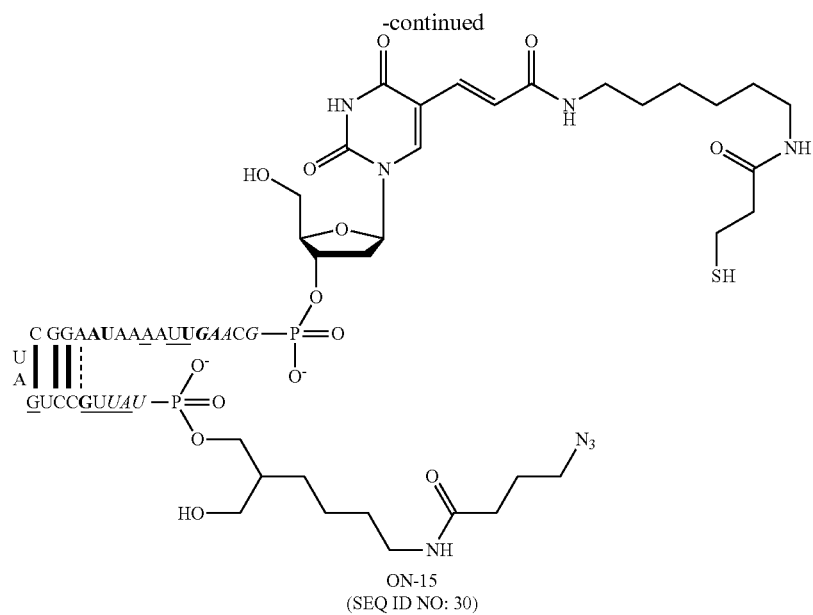
ON-15
(SEQ ID NO: 30)
An alkyne is introduced at 5'-end of tracrgRNA2 as represented by a non-limiting example of ON-16:
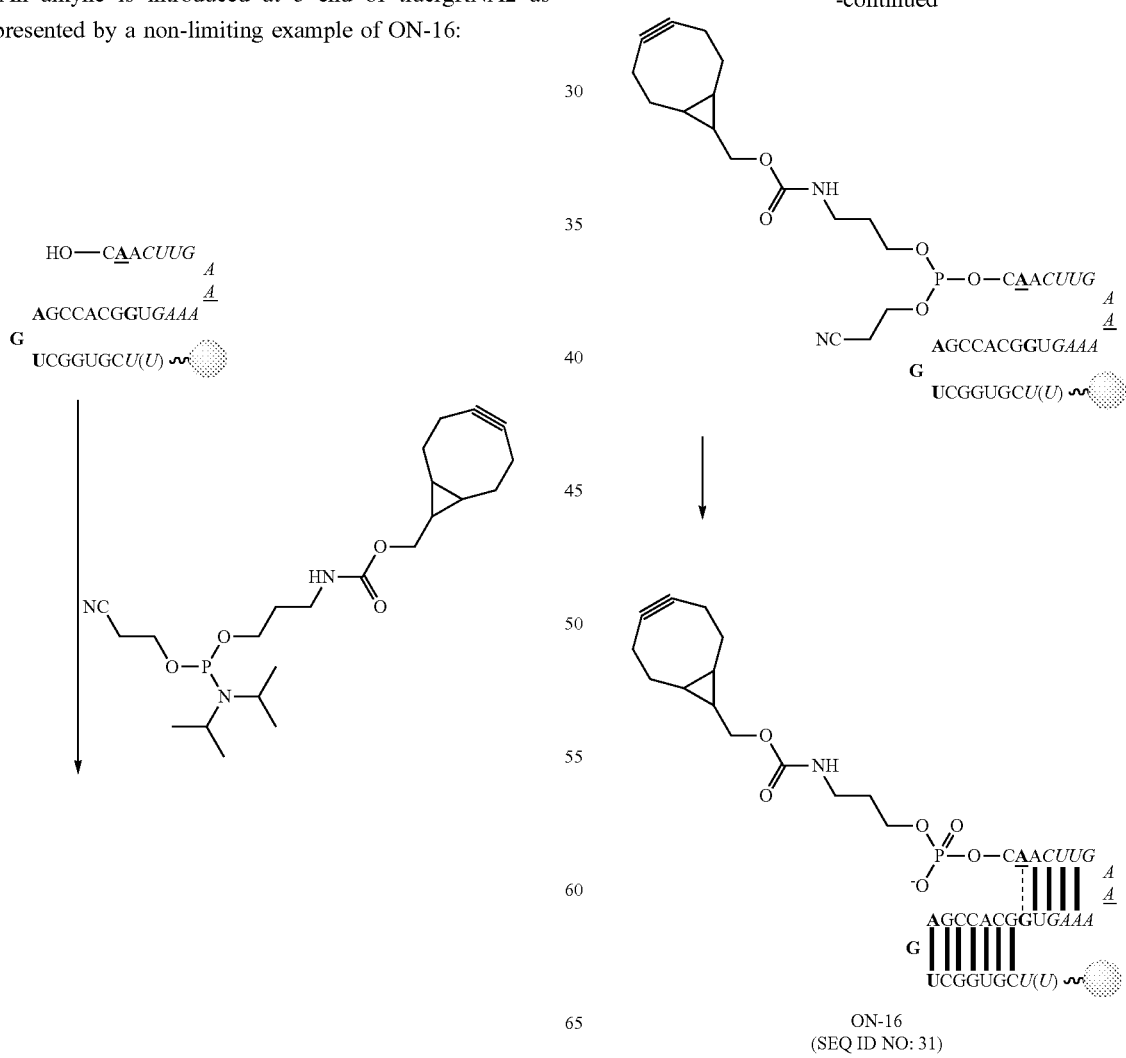
ON-16
(SEQ ID NO: 31)

TracrgRNA1, tracrgRNA2, and crgRNA are then ligated, and annealed as represented by a non-limiting example of ON-17:
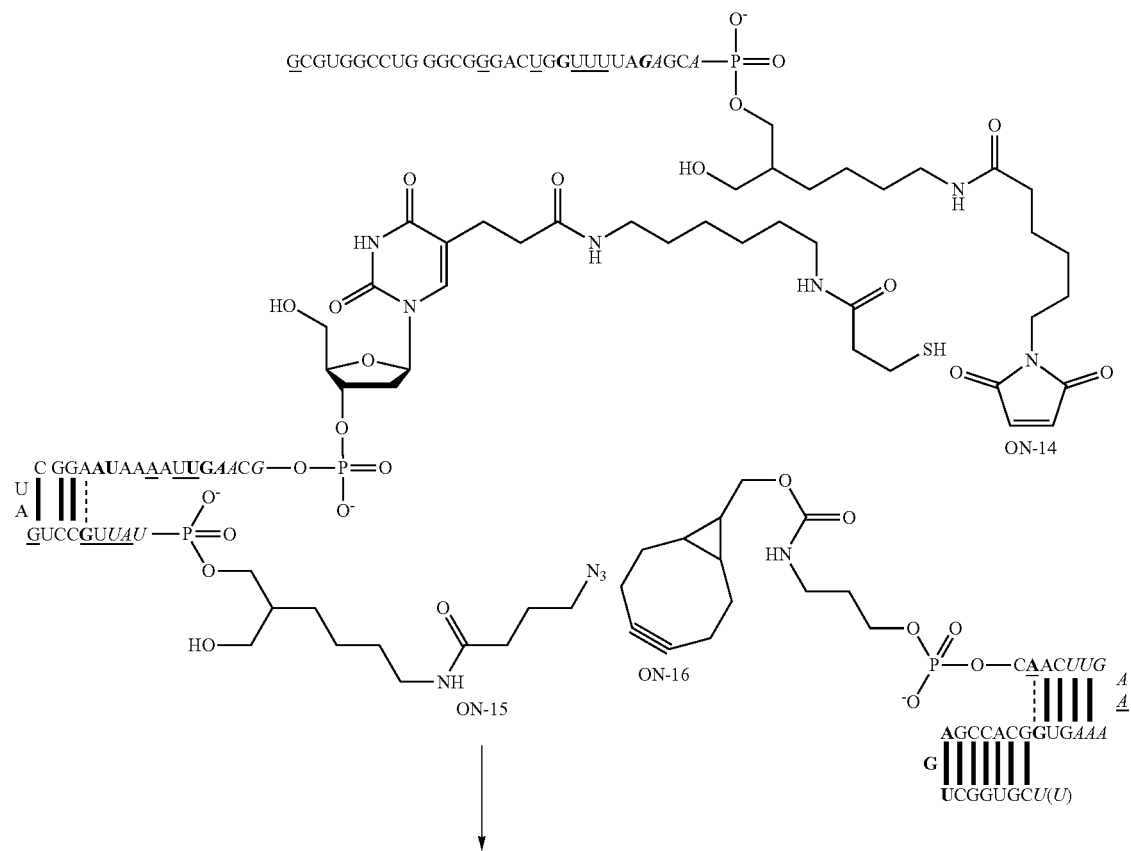

-continued

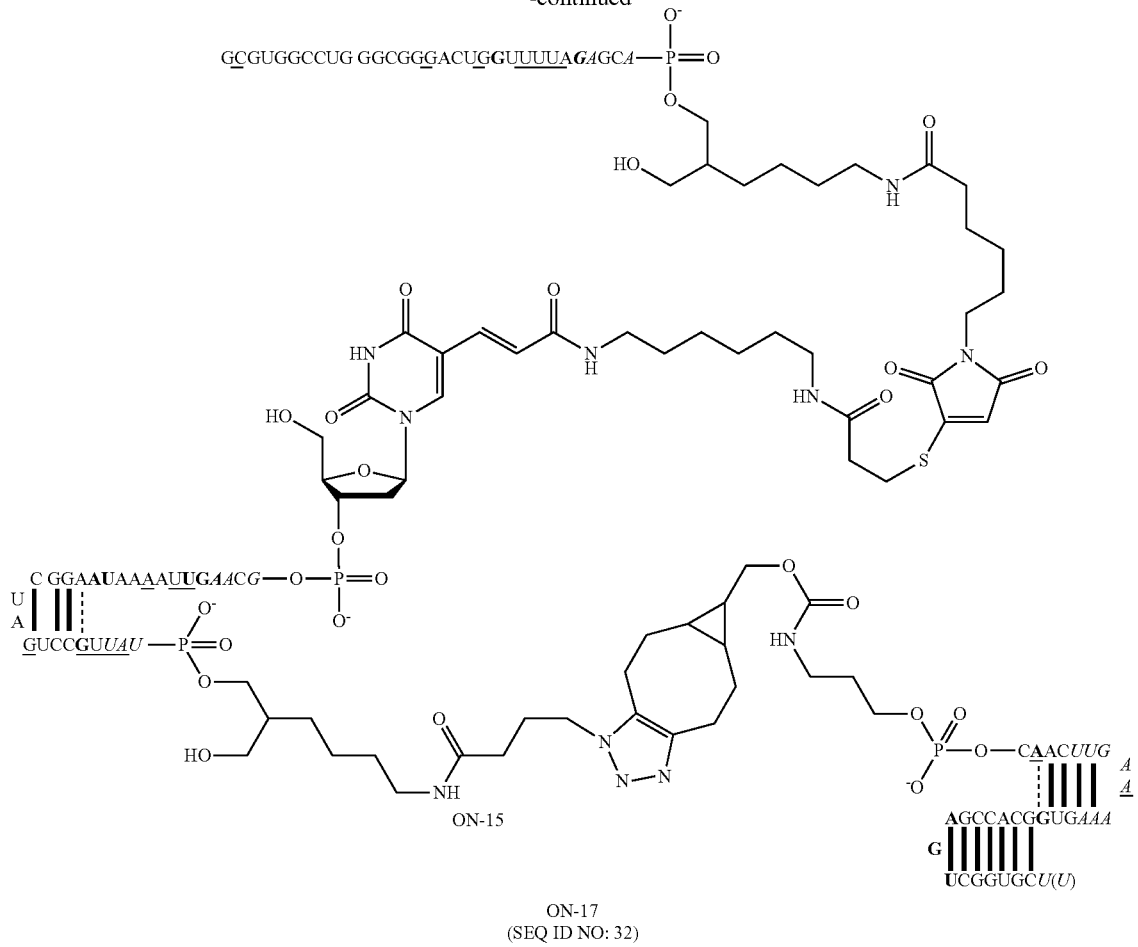

ON-17
(SEQ ID NO: 32)

In some embodiments, the ligation in tracrgRNA (ligation2) and the ligation between crgRNA and tracrgRNA (ligation1) are orthogonal, and two ligations are realized in two sequential steps.

In other embodiments, the ligation in tracrgRNA (ligation2) and the ligation between crgRNA and tracrgRNA (ligation1) are formed by the same ligation chemistry, and two ligations are realized sequentially as represented by synthesis of ON-20:

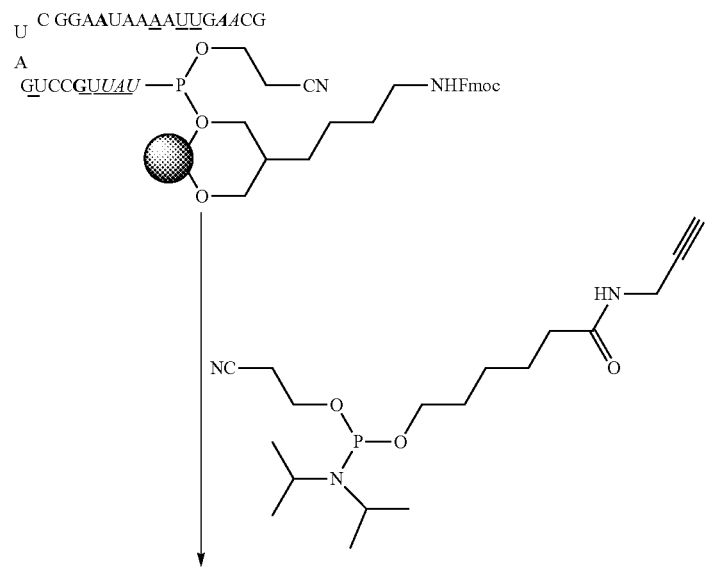
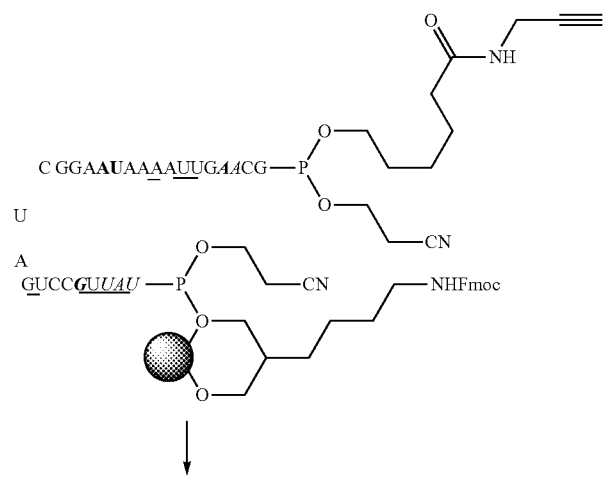
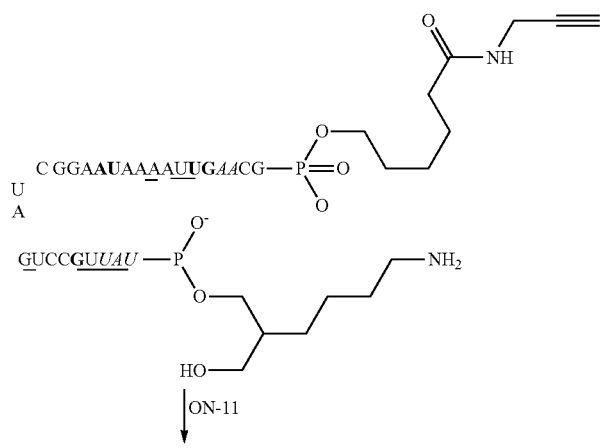

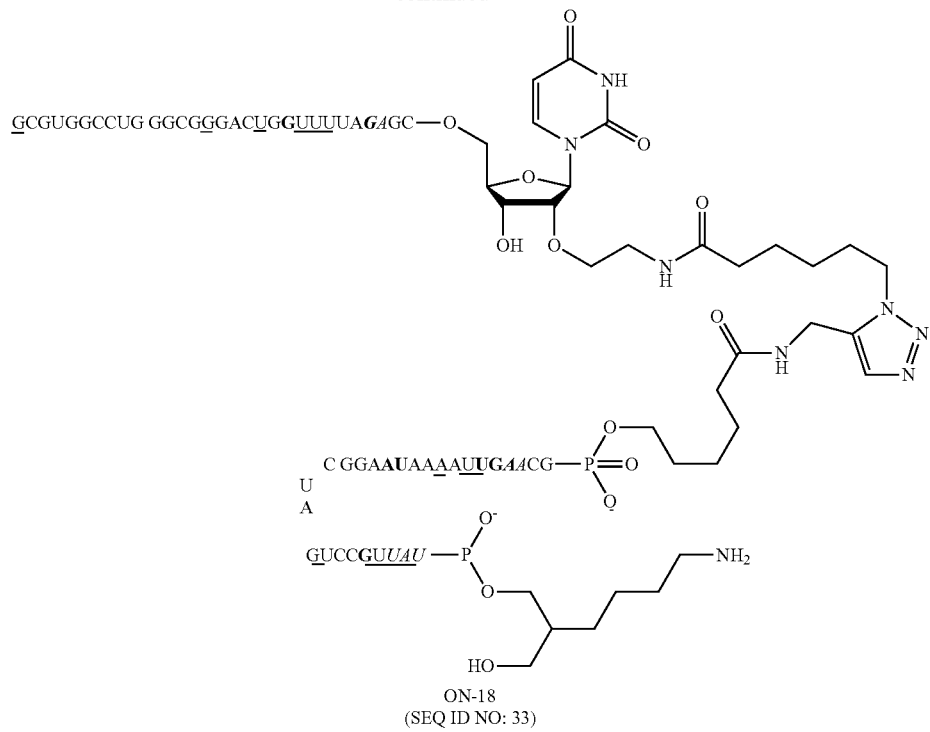
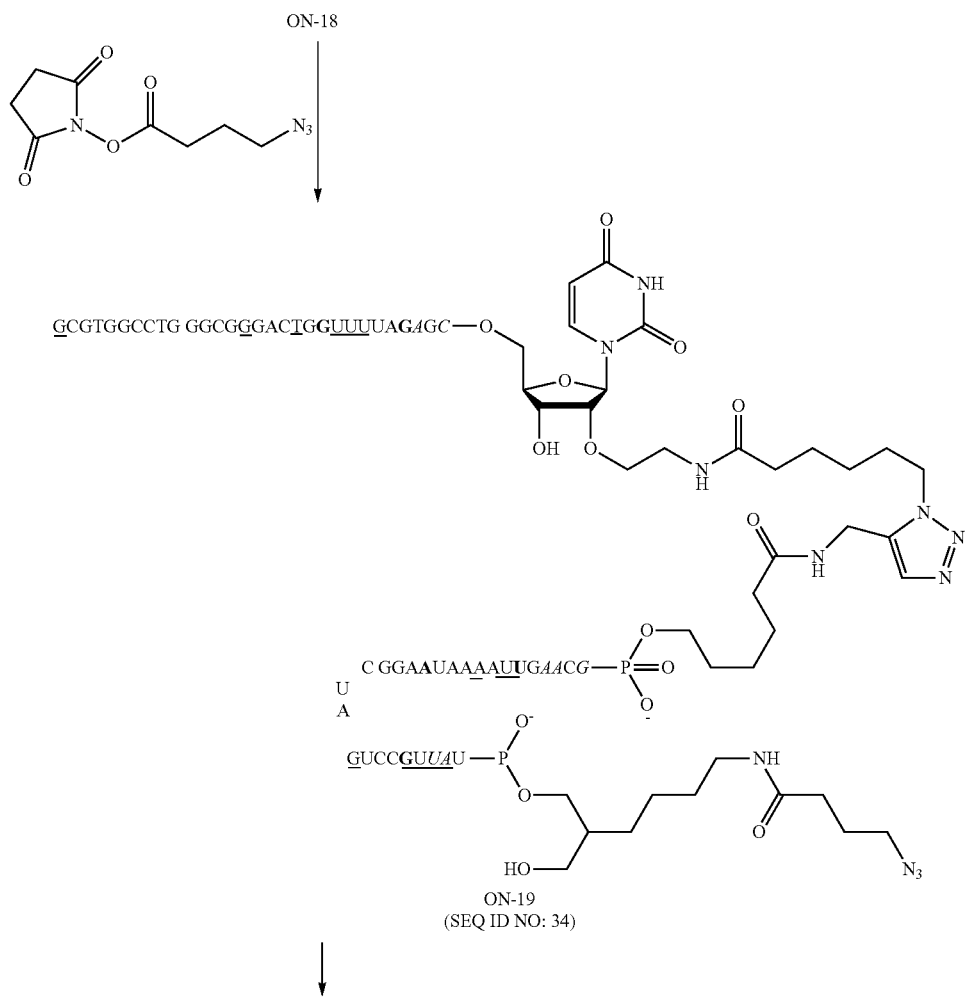

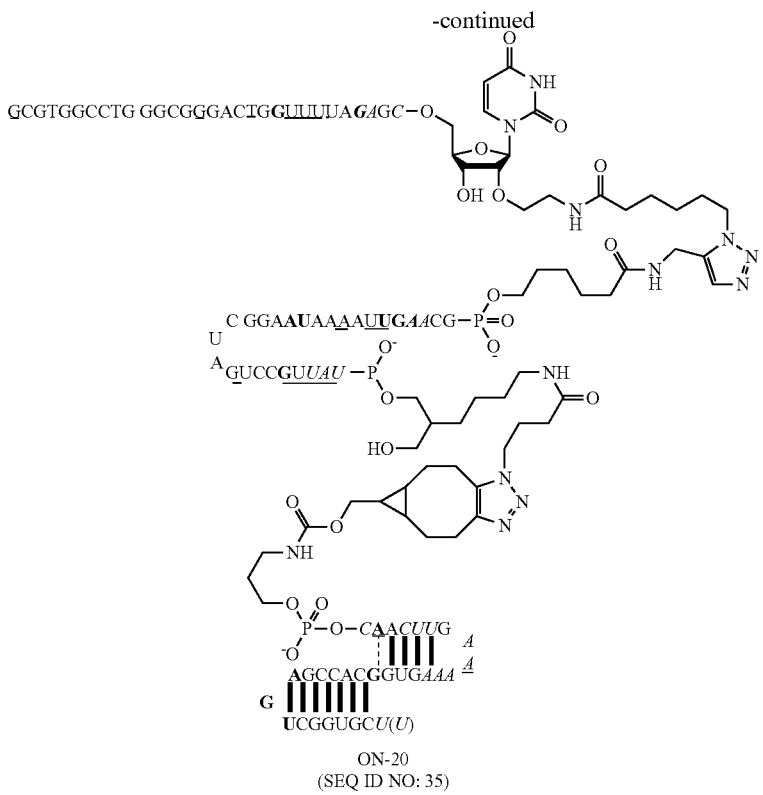

ON-20
(SEQ ID NO: 35)

Formation of Cas9-lgRNA, Cellular Transfections, and Assays

The formation of Cas9-lgRNA complex, and cellular transfections are performed as reported.

a. Transfection with cationic lipids (Liu, D. et al. Nature Biotechnology 2015, 33, 73-80):

Purified synthetic lgRNA or mixture of synthetic lgRNAs is incubated with purified Cas9 protein for 5 min, and then complexed with the cationic lipid reagent in 25 μL OPTIMEM. The resulting mixture is applied to the cells for 4 h at 37° C.

b. Transfection with cell-penetrating peptides (Kim, H. et al. Genome Res. 2014, 24: 1012-1019):

Cell-penetrating peptide (CPP) is conjugated to a purified recombinant Cas9 protein (with appended Cys residue at the C terminus) by drop wise mixing of 1 mg Cas9 protein (2 mg/mL) with 50 μg 4-maleimidobutyryl-GG-GRRRRRRRRRLLLL (m9R, SEQ ID NO: 58; 2 mg/mL) in PBS (pH 7.4) followed by incubation on a rotator at room temperature for 2 h. To remove unconjugated 9mR, the samples are dialyzed against DPBS (pH 7.4) at 4° C. for 24 h using 50 kDa molecular weight cutoff membranes. Cas9-m9R protein is collected from the dialysis membrane and the protein concentration is determined using the Bradford assay (Biorad).

Synthetic lgRNA or a mixture of synthetic lgRNAs is complexed with CPP:lgRNA (1 mg) in 1 μl of deionized water is gently added to the C3G9R4LC peptide (9R, SEQ ID NO: 59) in lgRNA:peptide weight ratios that range from 1:2.5 to 1:40 in 100 μl of DPBS (pH 7.4). This mixture is incubated at room temperature for 30 min and diluted 10-fold using RNase free deionized water.

150 μl Cas9-m9R (2 μM) protein is mixed with 100 μl lgRNA:9R (10:50 μg) complex and the resulting mixture is applied to the cells for 4 h at 37° C. Cells can also be treated with Cas9-m9R and lgRNA:9R sequentially.

The antiviral assay is performed according to reported procedures (Hu, W. et al. Proc Natl Acad Sci USA 2014, 110: 11461-11466; Lin, Su. et al. Molecular Therapy—Nucleic Acids, 2014, 3, e186). Delivery to cell lines is based either cationic lipid or CPP based delivery of Cas9-lgRNA complexes instead of plasmid transfection/transduction using gRNA/Cas9 expression vectors.

EXAMPLES

The following examples further illustrate embodiments of the disclosed invention, which are not limited by these examples.

Example 1: Compound 4

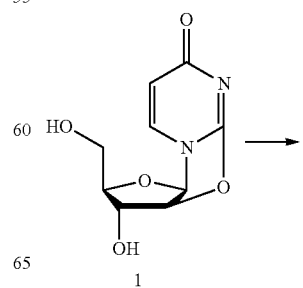

1

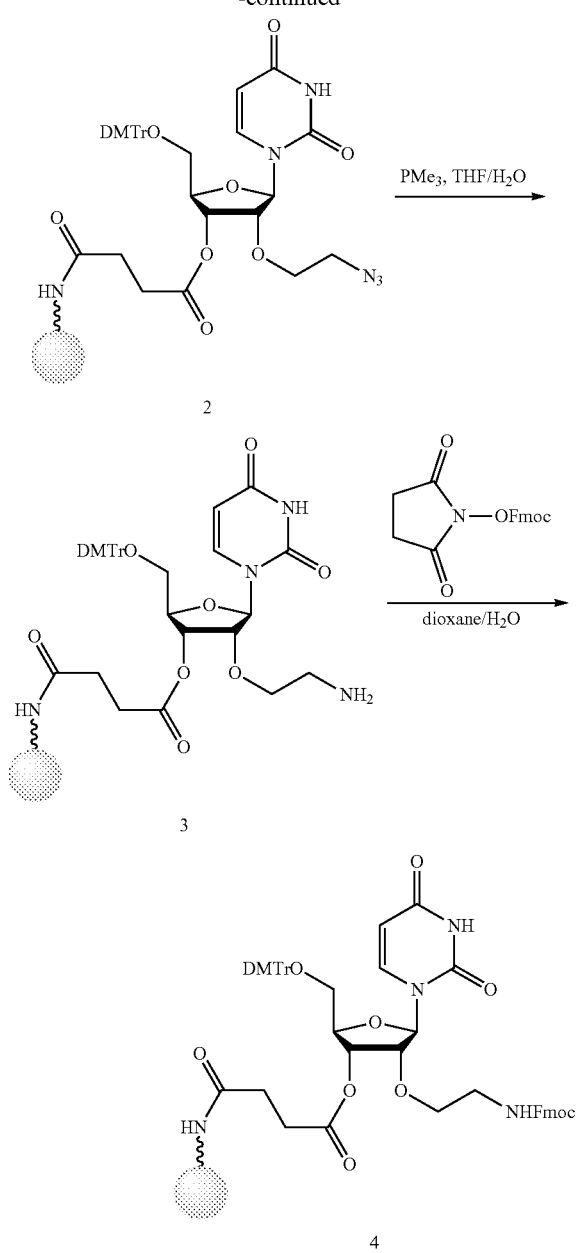

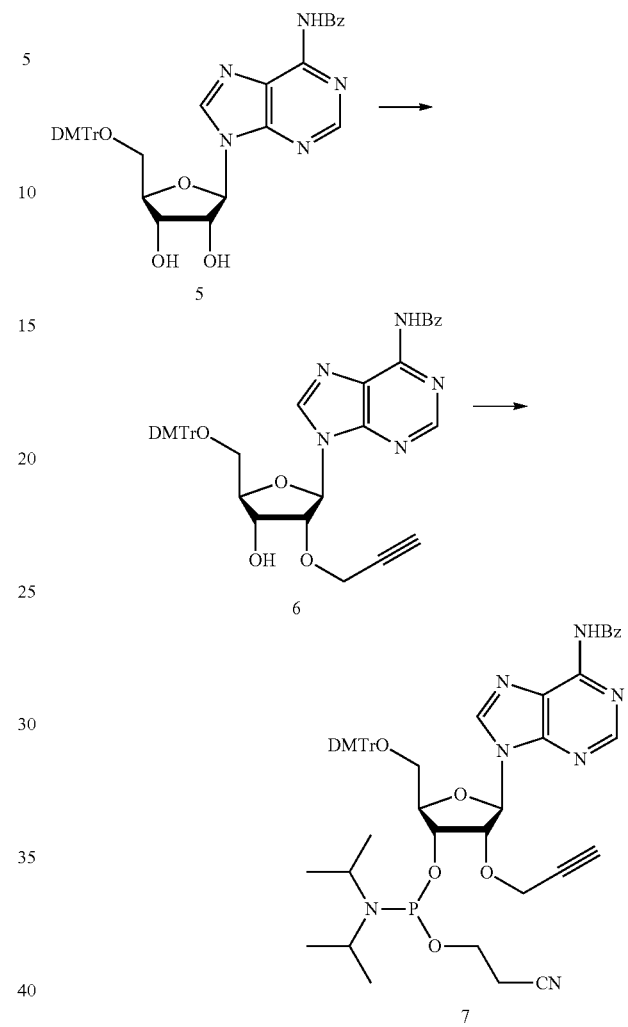

Example 2: Compound 7

Compound 2 is prepared essentially according to a reported procedure in 4 steps (Santner, T. et al. Bioconjugate Chem. 2014, 25, 188-195). Compound 1 is treated with 2-azidoethanol in dimethylacetamide at 120° C. at the presence of BF$_3$OEt$_2$, and the resulting 2'-azido nucleoside is tritylated (DMTrCl, in pyridine, RT), and attached to an amino-functionalized support.

To compound 2 (0.99 mmol) in THF/H$_2$O (2:1) (18 mL) is then added trimethylphosphine (1.5 mL, 1.5 mmol). Reaction is shaken at room temperature for 8 h and washed thoroughly with THF/H$_2$O (2:1). Dioxane/H$_2$O (1:1) (20 mL) and NaHCO$_3$ (185 mg, 2.2 mmol) are added. The reaction mixture is cooled down to 0° C., and Fmoc-OSu (415 mg, 1.23 mmol) in dioxane (2 mL) is added. The reaction is shaked for 15 min at 0° C., and then washed with water and then THF (3×20 mL) to give compound 4.

6-Benzoyl-5'-O-DMTr-adenosine 5 (1.24 g, 1.84 mmole) is dissolved in THF (40 mL) and sodium hydride (60% dispersion in mineral oil, 0.184 g, 4.6 mmole) is added in portions at 0° C. The reaction mixture is warmed up to room temperature and stirred for 15 min. The reaction is then cooled to 0° C., and propargyl bromide (80% in toluene, 0.44 mL, 3.98 mmole) is added. The reaction is then stirred under reflux for 12 h. Saturated aqueous sodium bicarbonate (10 mL) is added, and volatiles are removed in vacuo. The resulting residue is dissolved in DCM, and washed with water and saturated brine. The organic layer is collected, dried over anhydrous sodium sulfate, and concentrated till dryness in vacuo. The resulting residue is purified by silica-gel chromatography (eluent: 97:3, DCM:MeOH, 0.5% pyridine) to provide compound 6.

To a solution of compound 6 (0.30 g, 0.42 mmol) in anhydrous dichloromethane (5 mL) and diisopropylethyl-amine (0.15 mL, 0.83 mmol), under nitrogen, is added 2-cyanoethyl-N,N-diisopropyl-chlorophosphoramidite (0.13 mL, 0.58 mmol) dropwise. The reaction is stirred at room temperature for 3 h, and then diluted with dichloromethane (25 mL). The resulting solution is washed with saturated aqueous KCl (25 mL), dried from anhydrous Na$_2$SO$_4$, and concentrated in vacuo. The residue is purified by column chromatography (60% EtOAc/hexane, 0.5% pyridine) to give compound 7.

Example 3: ON-11

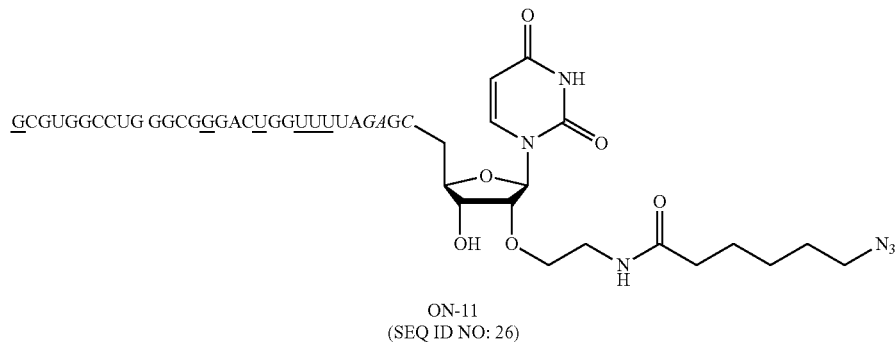

ON-11
(SEQ ID NO: 26)

ON-11 is prepared using 2'-TBS protected RNA phosphoramidite monomers with t-butylphenoxyacetyl protection of the A, G and C nucleobases and unprotected uracil. 0.3 M Benzylthiotetrazole in acetonitrile (Link Technologies) is used as the coupling agent, t-butylphenoxyacetic anhydride as the capping agent and 0.1 M iodine as the oxidizing agent. Oligonucleotide synthesis is carried out on an Applied Biosystems 394 automated DNA/RNA synthesizer using the standard 1.0 μmole RNA phosphoramidite cycle. Compound 4 (20 mg) is packed into a twist column. All β-cyanoethyl phosphoramidite monomers are dissolved in anhydrous acetonitrile to a concentration of 0.1 M immediately prior to use. Stepwise coupling efficiencies are determined by automated trityl cation conductivity monitoring and in all cases are >96.55%.

Fmoc is then cleaved by treatment with 20% piperidine in DMF. The resulting 3'-end aminoethyl oligonucleotide is then treated with NHS ester of 6-azido caproic acid in DMF.

Cleavage of oligonucleotides from the solid support and deprotection are achieved by exposure to concentrated aqueous ammonia/ethanol (3/1 v/v) for 2 h at room temperature followed by heating in a sealed tube for 45 min at 55° C. and desilylation in 1.0 M TBAF in THF for 24 h.

The above resulting oligonucleotide is dissolved in 0.5 M $Na_2CO_3$/$NaHCO_3$ buffer (pH 8.75) and incubated with succinimidyl-6-azidohexanate (20 eq.) in DMSO to give ON-11.

Purification of the oligonucleotide is carried out by reversed-phase HPLC on a Gilson system using an XBridge™ BEH300 Prep C18 10 μM 10×250 mm column (Waters) with a gradient of acetonitrile in ammonium acetate (0% to 50% buffer B over 30 min, flow rate 4 mL/min), buffer A: 0.1 M ammonium acetate, pH 7.0, buffer B: 0.1 M ammonium acetate, pH 7.0, with 50% acetonitrile. Elution is monitored by UV absorption at 295 nm. After HPLC purification, the oligonucleotide is desalted using an NAP-10 column.

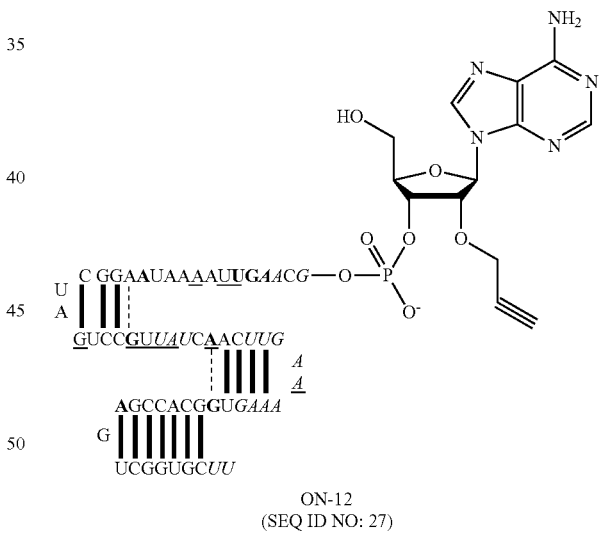

ON-12
(SEQ ID NO: 27)

Example 4: ON-12

ON-12 is synthesized in a way similar to the synthesis of ON-11, except that commercially available solid phase supported uridine phosphoramidite is used, and the last nucleoside phosphoramidite is compound 7.

The oligonucleotide is cleaved off the solid phase and fully deprotected, and purified as in example 3.

Example 5: ON-13

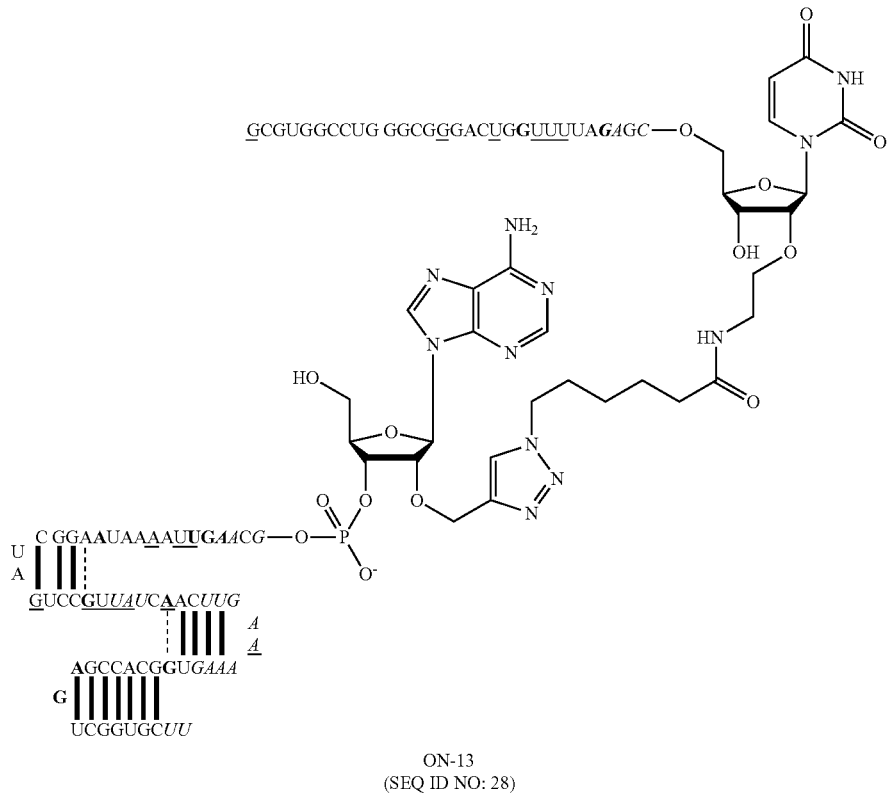

ON-13
(SEQ ID NO: 28)

A solution of alkyne ON-12 and azide ON-11 (0.2 nmol of each) in 0.2 M NaCl (50 μL) is annealed for 30 min at room temperature. In the meantime tris-hydroxypropyl triazole ligand (28 nmol in 42 μL 0.2 M NaCl), sodium ascorbate (40 nmol in 4 μL 0.2 M NaCl) and $CuSO_4.5H_2O$ (4 nmol in 4.0 μL 0.2 M NaCl), are added under argon. The reaction mixture is kept under argon at room temperature for the desired time, and formamide (50 μL) is added. The reaction is analyzed by and loading directly onto a 20% polyacrylamide electrophoresis gel, and purified by reversed-phase HPLC.

Example 6: ON-17

The ON-14 oligonucleotide carrying a maleimido group is incubated with 5'-SH-oligonucleotide (ON-15, 1:1 molar ratio) in 0.1 M triethylammonium acetate (TEAA) at pH 7.0 overnight at room temperature. The solution is evaporated to dryness, and to the resulting mixture is added ON-16 in 250 μM final concentration in phosphate-buffered saline (PBS), pH 7.4, containing 0.7% DMF and incubated at room temperature. The reaction mixture is analyzed and separated by HPLC to give ON-17.

Example 7: Cas9::ON-13 Complex

Cas9 protein: Recombinant Cas9 protein is available from New England BioLabs, Inc. and other providers or purified from E. coli by a routinely used protocol (Anders, C. and Jinek, M. Methods Enzymol. 2014, 546, 1-20). The purity and concentration of Cas9 protein are analyzed by SDS-PAGE.

Cas9-Lgrna Complex:
Cas9 and lgRNA are preincubated in a 1:1 molar ratio in the cleavage buffer to reconstitute the Cas9-lgRNA complex.

---

What is claimed is:

1. A method of cleaving a herpesvirus linear DNA, episomal DNA and DNA chromosomally integrated into the genome of a host cell, including the steps of:
   a) treating the host cell infected with herpesviruses with a composition comprising a Clustered Regularly Interspaced Short Palindromic Repeat (CRISPR)-associated endonuclease, and at least one lgRNA having a spacer sequence that is complementary to a target sequence in a herpesvirus genome; and
   b) cleaving said herpesvirus linear DNA, episomal DNA and integrated DNA, wherein said lgRNA comprises one or more internal non-nucleotide linkers.

2. The method according to claim 1, wherein said at least one lgRNA comprises a nucleic acid sequence complementary to a target nucleic acid sequence having a sequence identity of at least 75% to one sequence selected from the group comprising SEQ ID NOs: 51-57.

3. The method according to claim 1, wherein said lgRNA further comprises short peptide motifs of nuclear localization signals targeting nucleus, and said short peptide motifs are attached at its 5'- and/or 3'-end, and/or ligation sites of said lgRNA.

4. The method according to claim 1, wherein said lgRNA further comprises small molecular ligands, and said small molecular ligands are attached at 5'- and/or 3'-end, and/or ligation sites of said lgRNA.

5. The method according to claim 1, wherein said lgRNA comprises a spacer in crgRNA selected from sequences in the sense strand (5'→3') of herpesvirus genomes, and namely its RNA transcript, or the antisense strand (5'→3') of said herpesvirus genome, and namely its antisense RNA transcript.

6. The method according to claim 1, wherein said composition comprises at least two lgRNAs, for contacting and cleaving the target sequence(s) in herpesvirus genome.

7. The method according to claim 1, wherein said at least one lgRNA comprises a nucleic acid sequence complementary to a target nucleic acid sequence having a sequence identity of at least 75% to one or more target sequences from the RS1 gene or a conserved homolog thereof in HSV-1 and HSV-2.

8. The method according to claim 1, wherein said at least one lgRNA comprises a nucleic acid sequence complementary to a target nucleic acid sequence having a sequence identity of at least 75% to one or more target sequences from the UL30 gene or a conserved homolog thereof in HSV-1 and HSV-2.

9. The method according to claim 1, wherein said at least one lgRNA comprises a nucleic acid sequence complementary to a target nucleic acid sequence having a sequence identity of at least 75% to one or more target sequences from the RL1 gene or a conserved homolog thereof in HSV-1 and HSV-2.

10. The method according to claim 1, wherein said at least one lgRNA comprises a nucleic acid sequence complementary to a target nucleic acid sequence having a sequence identity of at least 75% to one or more target sequence from the UL5 and UL54 genes or a conserved homolog thereof in HSV-1 and HSV-2.

11. The method according to claim 1, wherein said composition comprises mixtures of lgRNAs with various spacers targeting different loci of target herpesvirus genome, and/or to variants of a single locus of target herpesvirus genome.

12. The method according to claim 1, wherein said composition comprises cationic lipids for therapeutic delivery to animal or human cells.

13. The method according to claim 1, wherein said composition comprises cell-penetrating peptide (CPP) for therapeutic delivery to animal or human cells.

14. The method according to claim 1, wherein said composition comprises transfecting agents for therapeutic delivery to host human cells.

15. The method according to claim 1, wherein said composition comprises at least one CRISPR-associated-proteins.

16. The method according to claim 1, wherein said composition comprises recombinant engineered Cas9 protein.

17. The method according to claim 1, wherein said composition is used in combination with direct antiviral agents.

18. The method according to claim 1, wherein said composition is used in combination with direct antiviral agents selected from acyclovir, ganciclovir, foscarnet, cidofovir, famciclovir, valganciclovir, and valaciclovir.

19. The method according to claim 1, wherein said CRISPR-associated endonuclease is replaced with a nucleic acid sequence encoding the said endonuclease.

20. A kit for the treatment of herpesvirus infection, including a measured amount of a composition comprising at least one isolated nucleic acid sequence encoding a Clustered Regularly Interspaced Short Palindromic Repeat (CRISPR)-associated endonuclease or CRISPR endonuclease, and at least one lgRNA, wherein each of said one or more lgRNAs includes a spacer sequence complementary to a target sequence of a herpesvirus DNA, and one or more items selected from the group consisting of packaging material, a package insert comprising instructions for use, a sterile fluid, a syringe and a sterile container.

21. A method of eliminating linear viral DNA, episomal DNA and integrated viral DNA from ex vivo cultured host cells infected with herpesvirus, including the steps of:
   a) obtaining a population of host cells latently from a patient infected with herpesvirus;
   b) culturing the host cells ex vivo;
   c) treating the host cells with a composition comprising a Clustered Regularly Interspaced Short Palindromic Repeat (CRISPR)-associated endonuclease, and at least one lgRNA having a spacer sequence that is complementary to a target sequence in said herpesvirus DNA;
   d) cleaving said herpesvirus genome;
   e) infusing the herpesvirus-eliminated cell population into the patient; and
   f) treating the patient.

22. The method according to claim 21, wherein said step of obtaining a population of host cells is further defined as obtaining a population of sensory neurons.

* * * * *

SEQUENCE LISTING

```
<160> NUMBER OF SEQ ID NOS: 59

<210> SEQ ID NO 1
<211> LENGTH: 94
<212> TYPE: RNA
<213> ORGANISM: Artificial Sequence
<220> FEATURE:
<223> OTHER INFORMATION: lgRNA, nn is either base-paired  or not, and
      joined by non-nucleotide linker between the two, n32 (A) and n33
      (B).
```

```
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u

<400> SEQUENCE: 1
nnnnnnnnnn nnnnnnnnnn guuuuagagc unnagcaagu uaaaauaagg cuaguccguu      60
aucaacuuga aaaaguggca ccgagucggu gcuu                                  94

<210> SEQ ID NO 2
<211> LENGTH: 62
<212> TYPE: RNA
<213> ORGANISM: Artificial Sequence
<220> FEATURE:
<223> OTHER INFORMATION: tracrgRNA: 5'-alkynyl tracrRNA, synthetic
      oligonucleotides

<400> SEQUENCE: 2
uagcaaguua aaauaaggcu aguccguuau caacuugaaa aaguggcacc gagucggugc      60
uu                                                                    62

<210> SEQ ID NO 3
<211> LENGTH: 32
<212> TYPE: RNA
<213> ORGANISM: Artificial Sequence
<220> FEATURE:
<223> OTHER INFORMATION: crgRNA: 3'-azido crRNA, synthetic
      oligonucleotides
<220> FEATURE:
<221> NAME/KEY: misc_feature
<222> LOCATION: (1)..(20)
<223> OTHER INFORMATION: n is a, c, g, or u

<400> SEQUENCE: 3
nnnnnnnnnn nnnnnnnnnn guuuuagagc ua                                    32

<210> SEQ ID NO 4
<211> LENGTH: 94
<212> TYPE: RNA
<213> ORGANISM: Artificial Sequence
<220> FEATURE:
<223> OTHER INFORMATION: lgRNA: crRNA and tracrRNA are fused as a single
      whole RNA by nNt-linker between a32 and u33.
<220> FEATURE:
<221> NAME/KEY: misc_feature
<222> LOCATION: (1)..(20)
<223> OTHER INFORMATION: n is a, c, g, or u

<400> SEQUENCE: 4
nnnnnnnnnn nnnnnnnnnn guuuuagagc uauagcaagu uaaaauaagg cuaguccguu      60
aucaacuuga aaaaguggca ccgagucggu gcuu                                  94

<210> SEQ ID NO 5
<211> LENGTH: 42
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: n is a, c, g, or u

<400> SEQUENCE: 5
nnnnnnnnnn nnnnnnnnnn guuuuagagc uaugcuguuu ug                         42
```

```
<210> SEQ ID NO 6
<211> LENGTH: 81
<212> TYPE: RNA
<213> ORGANISM: Streptococcus pyogenes

<400> SEQUENCE: 6
ggaaccauuc aaaacagcau agcaaguuaa aauaaggcua guccguuauc aacuugaaaa      60
aguggcaccg agucggugcu u                                                81

<210> SEQ ID NO 7
<211> LENGTH: 94
<212> TYPE: RNA
<213> ORGANISM: Artificial Sequence
<220> FEATURE:
<223> OTHER INFORMATION: lgRNA formed by two ligations between nn of
      crgRNA and tracrgRNA, and between a71 and a72 in tracrgRNA.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u

<400> SEQUENCE: 7
nnnnnnnnnn nnnnnnnnnn guuuuagagc unnagcaagu uaaaauaagg cuaguccguu      60
aucaacuuga aaaguggca ccgagucggu gcuu                                   94

<210> SEQ ID NO 8
<211> LENGTH: 94
<212> TYPE: RNA
<213> ORGANISM: Artificial Sequence
<220> FEATURE:
<223> OTHER INFORMATION: lgRNA formed by two ligations between nn of
      crgRNA and tracrgRNA, and between u62 and c63 in tracrgRNA.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u

<400> SEQUENCE: 8
nnnnnnnnnn nnnnnnnnnn guuuuagagc unnagcaagu uaaaauaagg cuaguccguu      60
aucaacuuga aaaguggca ccgagucggu gcuu                                   94

<210> SEQ ID NO 9
<211> LENGTH: 94
<212> TYPE: RNA
<213> ORGANISM: Artificial Sequence
<220> FEATURE:
<223> OTHER INFORMATION: lgRNA formed by three ligations between nn of
      crgRNA and tracrgRNA, between a71 and a72, and between g85 and u86
      in tracrgRNA.
<220> FEATURE:
<221> NAME/KEY: Modified
<222> LOCATION: (1)..(20)
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u
```

```
<400> SEQUENCE: 9
nnnnnnnnnn nnnnnnnnnn guuuuagagc unnagcaagu uaaaauaagg cuaguccguu    60
aucaacuuga aaaguggca ccgagucggu gcuu                                 94

<210> SEQ ID NO 10
<211> LENGTH: 74
<212> TYPE: RNA
<213> ORGANISM: Artificial Sequence
<220> FEATURE:
<223> OTHER INFORMATION: Truncated lgRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (32)..(33)
<223> OTHER INFORMATION: n is a, c, g, or u

<400> SEQUENCE: 10
nnnnnnnnnn nnnnnnnnnn guuuuagagc unnagcaagu uaaaaggcua guccguuauc    60
aacuugaaaa agug                                                     74

<210> SEQ ID NO 11
<211> LENGTH: 78
<212> TYPE: RNA
<213> ORGANISM: Artificial Sequence
<220> FEATURE:
<223> OTHER INFORMATION: Truncated lgRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (30)..(31)
<223> OTHER INFORMATION: n is a, c, g, or u

<400> SEQUENCE: 11
nnnnnnnnnn nnnnnnnnnn guuuuagagn ncaaguuaaa auaaggcuag uccguuauca    60
auggcaccga gucggugc                                                 78

<210> SEQ ID NO 12
<211> LENGTH: 75
<212> TYPE: RNA
<213> ORGANISM: Artificial Sequence
<220> FEATURE:
<223> OTHER INFORMATION: Truncated lgRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (31)..(32)
<223> OTHER INFORMATION: n is a, c, g, or u

<400> SEQUENCE: 12
nnnnnnnnnn nnnnnnnnnn guuuuagagc nnguuaaaau aaggcuaguc cguuaucaau    60
ggaccgaguc ggugc                                                    75

<210> SEQ ID NO 13
<211> LENGTH: 74
<212> TYPE: RNA
<213> ORGANISM: Artificial Sequence
<220> FEATURE:
<223> OTHER INFORMATION: Truncated lgRNA
```

```
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (29)..(30)
<223> OTHER INFORMATION: n is a, c, g, or u

<400> SEQUENCE: 13
nnnnnnnnnn nnnnnnnnnn guuuuagcnn guuaaaauaa ggcuaguccg uuaucaaugg    60
caccgagucg gugc                                                       74

<210> SEQ ID NO 14
<211> LENGTH: 73
<212> TYPE: RNA
<213> ORGANISM: Artificial Sequence
<220> FEATURE:
<223> OTHER INFORMATION: Truncated lgRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (31)..(32)
<223> OTHER INFORMATION: n is a, c, g, or u

<400> SEQUENCE: 14
nnnnnnnnnn nnnnnnnnnn guuuuagagc nnguuaaaau aaggcuaguc cguaaauggc    60
accgagucgg ugc                                                        73

<210> SEQ ID NO 15
<211> LENGTH: 67
<212> TYPE: RNA
<213> ORGANISM: Artificial Sequence
<220> FEATURE:
<223> OTHER INFORMATION: Truncated lgRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (29)..(30)
<223> OTHER INFORMATION: n is a, c, g, or u

<400> SEQUENCE: 15
nnnnnnnnnn nnnnnnnnnn guuuuagcnn guuaaaaggc uaguccguaa uggcaccgag    60
ucggugc                                                               67

<210> SEQ ID NO 16
<211> LENGTH: 30
<212> TYPE: RNA
<213> ORGANISM: Artificial Sequence
<220> FEATURE:
<223> OTHER INFORMATION: ON-1: 3'-amino crgRNA.

<400> SEQUENCE: 16
gcguggccug ggcgggacug guuuuagaga                                      30

<210> SEQ ID NO 17
<211> LENGTH: 30
<212> TYPE: RNA
<213> ORGANISM: Artificial Sequence
<220> FEATURE:
<223> OTHER INFORMATION: ON-2: 3'-azido crgRNA.
```

```
<400> SEQUENCE: 17
gcguggccug ggcgggacug guuuuagaga                              30

<210> SEQ ID NO 18
<211> LENGTH: 61
<212> TYPE: RNA
<213> ORGANISM: Artificial Sequence
<220> FEATURE:
<223> OTHER INFORMATION: ON-3: solid supported tracrgRNA after
      detritylation.

<400> SEQUENCE: 18
agcaaguuaa aauaaggcua guccguuauc aacuugaaaa aguggcaccg agucggugcu    60
u                                                                   61

<210> SEQ ID NO 19
<211> LENGTH: 61
<212> TYPE: RNA
<213> ORGANISM: Artificial Sequence
<220> FEATURE:
<223> OTHER INFORMATION: ON-4: solid supported 5'-alkynyl tracrgRNA
      before deprotection

<400> SEQUENCE: 19
agcaaguuaa aauaaggcua guccguuauc aacuugaaaa aguggcaccg agucggugcu    60
u                                                                   61

<210> SEQ ID NO 20
<211> LENGTH: 61
<212> TYPE: RNA
<213> ORGANISM: Artificial Sequence
<220> FEATURE:
<223> OTHER INFORMATION: ON-5: 5'-alkynyl tracrgRNA.

<400> SEQUENCE: 20
agcaaguuaa aauaaggcua guccguuauc aacuugaaaa aguggcaccg agucggugcu    60
u                                                                   61

<210> SEQ ID NO 21
<211> LENGTH: 61
<212> TYPE: RNA
<213> ORGANISM: Artificial Sequence
<220> FEATURE:
<223> OTHER INFORMATION: ON-6: solid supported 5'-alkynyl (strained)
      tracrgRNA before deprotection.

<400> SEQUENCE: 21
agcaaguuaa aauaaggcua guccguuauc aacuugaaaa aguggcaccg agucggugcu    60
u                                                                   61

<210> SEQ ID NO 22
<211> LENGTH: 61
<212> TYPE: RNA
<213> ORGANISM: Artificial Sequence
<220> FEATURE:
<223> OTHER INFORMATION: ON-7: 5'-alkynyl (strained) tracrgRNA.

<400> SEQUENCE: 22
agcaaguuaa aauaaggcua guccguuauc aacuugaaaa aguggcaccg agucggugcu    60
u                                                                   61
```

-continued

```
<210> SEQ ID NO 23
<211> LENGTH: 61
<212> TYPE: RNA
<213> ORGANISM: Artificial Sequence
<220> FEATURE:
<223> OTHER INFORMATION: ON-8: solid supported 5'-thiol tracrgRNA before
      deprotection.

<400> SEQUENCE: 23
agcaaguuaa aauaaggcua guccguuauc aacuugaaaa aguggcaccg agucggugcu    60
u                                                                   61

<210> SEQ ID NO 24
<211> LENGTH: 61
<212> TYPE: RNA
<213> ORGANISM: Artificial Sequence
<220> FEATURE:
<223> OTHER INFORMATION: ON-9: 5'-thiol tracrgRNA.

<400> SEQUENCE: 24
agcaaguuaa aauaaggcua guccguuauc aacuugaaaa aguggcaccg agucggugcu    60
u                                                                   61

<210> SEQ ID NO 25
<211> LENGTH: 30
<212> TYPE: RNA
<213> ORGANISM: Artificial Sequence
<220> FEATURE:
<223> OTHER INFORMATION: ON-10: 3'-maleimidyl crgRNA

<400> SEQUENCE: 25
gcguggccug ggcgggacug guuuuagagc                                    30

<210> SEQ ID NO 26
<211> LENGTH: 31
<212> TYPE: RNA
<213> ORGANISM: Artificial Sequence
<220> FEATURE:
<223> OTHER INFORMATION: ON-11: 3'-azido crgRNA.

<400> SEQUENCE: 26
gcguggccug ggcgggacug guuuuagagc u                                  31

<210> SEQ ID NO 27
<211> LENGTH: 61
<212> TYPE: RNA
<213> ORGANISM: Artificial Sequence
<220> FEATURE:
<223> OTHER INFORMATION: ON-12: 5'-alkynyl tracrgRNA.

<400> SEQUENCE: 27
agcaaguuaa aauaaggcua guccguuauc aacuugaaaa aguggcaccg agucggugcu    60
u                                                                   61

<210> SEQ ID NO 28
<211> LENGTH: 92
<212> TYPE: RNA
<213> ORGANISM: Artificial Sequence
<220> FEATURE:
<223> OTHER INFORMATION: ON-13: lgRNA ligated between 31u and 32a.

<400> SEQUENCE: 28
gcguggccug ggcgggacug guuuuagagc uagcaaguua aaauaaggcu aguccguuau    60
caacuugaaa aaguggcacc gagucggugc uu                                 92
```

```
<210> SEQ ID NO 29
<211> LENGTH: 31
<212> TYPE: RNA
<213> ORGANISM: Artificial Sequence
<220> FEATURE:
<223> OTHER INFORMATION: ON-14: 3'-maleimidyl crgRNA

<400> SEQUENCE: 29
gcguggccug ggcgggacug guuuuagagc a                              31

<210> SEQ ID NO 30
<211> LENGTH: 29
<212> TYPE: RNA
<213> ORGANISM: Artificial Sequence
<220> FEATURE:
<223> OTHER INFORMATION: ON-15: 5'-thiol 3'-azido tracrgRNA1

<400> SEQUENCE: 30
ugcaaguuaa aauaaggcua guccguuau                                 29

<210> SEQ ID NO 31
<211> LENGTH: 32
<212> TYPE: RNA
<213> ORGANISM: Artificial Sequence
<220> FEATURE:
<223> OTHER INFORMATION: ON-16: 5'-alkynyl tracrgRNA2.

<400> SEQUENCE: 31
caacuugaaa aaguggcacc gagucggugc uu                             32

<210> SEQ ID NO 32
<211> LENGTH: 92
<212> TYPE: RNA
<213> ORGANISM: Artificial Sequence
<220> FEATURE:
<223> OTHER INFORMATION: ON-17: lgRNA ligated between a31 and u32, and
      between u60 and c61.

<400> SEQUENCE: 32
gcguggccug ggcgggacug guuuuagagc augcaaguua aauaaggcu aguccguuau  60 caacuugaaa aaguggcacc gagucggugc uu                              92

<210> SEQ ID NO 33
<211> LENGTH: 59
<212> TYPE: RNA
<213> ORGANISM: Artificial Sequence
<220> FEATURE:
<223> OTHER INFORMATION: ON-18: 3'-amino ligated crgRNA and tracrgRNA1.

<400> SEQUENCE: 33
gcguggccug ggcgggacug guuuuagagc ugcaaguuaa aauaaggcua guccguuau  59

<210> SEQ ID NO 34
<211> LENGTH: 59
<212> TYPE: RNA
<213> ORGANISM: Artificial Sequence
<220> FEATURE:
<223> OTHER INFORMATION: ON-19: 3'-azido ligated crgRNA and tracrgRNA1.

<400> SEQUENCE: 34
gcguggccug ggcgggacug guuuuagagc ugcaaguuaa aauaaggcua guccguuau  59

<210> SEQ ID NO 35
<211> LENGTH: 91
<212> TYPE: RNA
<213> ORGANISM: Artificial Sequence
```

```
<220> FEATURE:
<223> OTHER INFORMATION: ON-20: lgRNA.

<400> SEQUENCE: 35
gcguggccug ggcgggacug guuuuagagc ugcaaguuaa aauaaggcua guccguuauc    60
aacuugaaaa aguggcaccg agucggugcu u                                  91

<210> SEQ ID NO 36
<211> LENGTH: 23
<212> TYPE: DNA
<213> ORGANISM: HBV

<400> SEQUENCE: 36
ctctgctaga tcccagagtg agg                                           23

<210> SEQ ID NO 37
<211> LENGTH: 23
<212> TYPE: DNA
<213> ORGANISM: HBV

<400> SEQUENCE: 37
gctatcgctg gatgtgtctg cgg                                           23

<210> SEQ ID NO 38
<211> LENGTH: 25
<212> TYPE: DNA
<213> ORGANISM: HBV

<400> SEQUENCE: 38
tggacttctc tcaattttct agggg                                         25

<210> SEQ ID NO 39
<211> LENGTH: 23
<212> TYPE: DNA
<213> ORGANISM: HBV

<400> SEQUENCE: 39 ggggatcac ccgtgtgtct tgg                                            23

<210> SEQ ID NO 40
<211> LENGTH: 25
<212> TYPE: DNA
<213> ORGANISM: HBV

<400> SEQUENCE: 40
tatgtggatg atgtggtact ggggg                                         25

<210> SEQ ID NO 41
<211> LENGTH: 21
<212> TYPE: DNA
<213> ORGANISM: HBV

<400> SEQUENCE: 41
cctcaccata cagcactcgg g                                             21

<210> SEQ ID NO 42
<211> LENGTH: 26
<212> TYPE: DNA
<213> ORGANISM: HBV

<400> SEQUENCE: 42
gtgttggggt gagttgatga atctgg                                        26
```

```
<210> SEQ ID NO 43
<211> LENGTH: 25
<212> TYPE: DNA
<213> ORGANISM: HIV

<400> SEQUENCE: 43
tatgtggatg atgtggtact ggggg                                  25

<210> SEQ ID NO 44
<211> LENGTH: 25
<212> TYPE: DNA
<213> ORGANISM: HIV

<400> SEQUENCE: 44
tatatggatg atgtggtatt ggggg                                  25

<210> SEQ ID NO 45
<211> LENGTH: 25
<212> TYPE: DNA
<213> ORGANISM: HIV

<400> SEQUENCE: 45
tatgtggatg atgtggtatt ggggg                                  25

<210> SEQ ID NO 46
<211> LENGTH: 25
<212> TYPE: DNA
<213> ORGANISM: HIV

<400> SEQUENCE: 46
tatatagatg atgtggtact ggggg                                  25

<210> SEQ ID NO 47
<211> LENGTH: 23
<212> TYPE: DNA
<213> ORGANISM: HIV

<400> SEQUENCE: 47
gattggcaga actacacacc agg                                    23

<210> SEQ ID NO 48
<211> LENGTH: 23
<212> TYPE: DNA
<213> ORGANISM: HIV

<400> SEQUENCE: 48
atcagatatc cactgacctt tgg                                    23

<210> SEQ ID NO 49
<211> LENGTH: 23
<212> TYPE: DNA
<213> ORGANISM: HIV

<400> SEQUENCE: 49
gcgtggcctg ggcgggactg ggg                                    23

<210> SEQ ID NO 50
<211> LENGTH: 23
<212> TYPE: DNA
<213> ORGANISM: HIV

<400> SEQUENCE: 50
cagcagttct tgaagtactc cgg                                    23
```

```
<210> SEQ ID NO 51
<211> LENGTH: 23
<212> TYPE: DNA
<213> ORGANISM: EBV

<400> SEQUENCE: 51
gccctggacc aacccggccc ggg                                              23

<210> SEQ ID NO 52
<211> LENGTH: 23
<212> TYPE: DNA
<213> ORGANISM: EBV

<400> SEQUENCE: 52
ggccgctgcc ccgctccggg tgg                                              23

<210> SEQ ID NO 53
<211> LENGTH: 22
<212> TYPE: DNA
<213> ORGANISM: EBV

<400> SEQUENCE: 53
ggaagacaat gtgccgccat gg                                               22

<210> SEQ ID NO 54
<211> LENGTH: 23
<212> TYPE: DNA
<213> ORGANISM: EBV

<400> SEQUENCE: 54
tctggaccag aaggctccgg cgg                                              23

<210> SEQ ID NO 55
<211> LENGTH: 23
<212> TYPE: DNA
<213> ORGANISM: EBV

<400> SEQUENCE: 55
gctgccgcgg agggtgatga cgg                                              23

<210> SEQ ID NO 56
<211> LENGTH: 23
<212> TYPE: DNA
<213> ORGANISM: EBV

<400> SEQUENCE: 56
ggtggcccac cgggtccgct ggg                                              23

<210> SEQ ID NO 57
<211> LENGTH: 23
<212> TYPE: DNA
<213> ORGANISM: EBV

<400> SEQUENCE: 57
gtcctcgagg gggccgtcgc ggg                                              23

<210> SEQ ID NO 58
<211> LENGTH: 16
<212> TYPE: PRT
<213> ORGANISM: Artificial Sequence
<220> FEATURE:
<223> OTHER INFORMATION: Cell-penetrating peptide, N-terninal modified
      with 4-maleimidobutyryl
```

```
<400> SEQUENCE: 58

Gly Gly Gly Arg Arg Arg Arg Arg Arg Arg Arg Leu Leu Leu Leu
1               5                   10                  15

<210> SEQ ID NO 59
<211> LENGTH: 18
<212> TYPE: PRT
<213> ORGANISM: Artificial Sequence
<220> FEATURE:
<223> OTHER INFORMATION: Cell-penetrating peptide, 9R

<400> SEQUENCE: 59

Cys Cys Cys Gly Gly Gly Gly Gly Gly Gly Gly Arg Arg Arg Arg
1               5                   10                  15

Leu Cys
```